United States Patent [19]

Hashimoto

[11] Patent Number: 4,486,391

[45] Date of Patent: Dec. 4, 1984

[54] SEPARATION AND RECOVERY OF IONIC SUBSTANCES BY FLUORINE-CONTAINING COMPOUND

[75] Inventor: Yutaka Hashimoto, Urawa, Japan

[73] Assignees: Dainippon Ink and Chemicals, Inc., Tokyo; Kawamura Institute of Chemical Research, Saitama, both of Japan

[21] Appl. No.: 409,305

[22] Filed: Aug. 18, 1982

[30] Foreign Application Priority Data

Aug. 25, 1981 [JP] Japan ........ 56-132049
Aug. 25, 1981 [JP] Japan ........ 56-132050
Aug. 25, 1981 [JP] Japan ........ 56-132051
Sep. 17, 1981 [JP] Japan ........ 56-145445
Apr. 21, 1982 [JP] Japan ........ 57-65498

[51] Int. Cl.[3] ........ B01D 11/04

[52] U.S. Cl. ........ 423/9; 75/101 BE; 210/638; 210/682; 210/688; 210/690; 210/729; 210/912; 423/8; 423/24; 562/554; 564/96

[58] Field of Search ........ 210/673, 681-688, 210/690, 691, 634, 638, 643, 729, 912; 75/101 BE; 423/6, 7, 24, 54, 63, 70, 100, 112, 157, 181, 8, 9; 562/554; 564/96, 209, 281; 570/126, 136, 141

[56] References Cited

U.S. PATENT DOCUMENTS 2,764,602 9/1956 Ahlbrecht ........ 564/209
2,990,417 6/1961 Carboni ........ 252/180
3,226,380 12/1965 Knight ........ 562/554
3,755,161 8/1973 Yokota et al. ........ 210/679
4,039,446 8/1977 Ban et al. ........ 210/688
4,238,328 12/1980 Bowes et al. ........ 210/688
4,252,959 2/1981 Spitzner ........ 423/24
4,277,565 7/1981 Oda et al. ........ 423/7
4,296,034 10/1981 Bouvet et al. ........ 564/96

FOREIGN PATENT DOCUMENTS 2018786 10/1979 United Kingdom .

*Primary Examiner*—Peter Hruskoci
*Attorney, Agent, or Firm*—Sherman & Shalloway

[57] ABSTRACT

A method for separating an ionic substance from a liquid medium, which comprises including a metal ion, a metal oxide ion, a metal complex ion, ammonium compounds, etc. dissolved or dispersed in the liquid medium by using a fluorine containing compound of the following formula $$[\{Rf\text{-}(A)_a\text{-}Y\}(X)_b]_n(Z)_c$$

containing a fluoroalkyl group (Rf) having 3 to 20 carbon atoms and a group (Y) having affinity for the ionic substances. A composition for trapping ionic substances, comprising the aforesaid fluorine-containing compound as a main ingredient. The invention can be advantageously applied to the recovery of useful metals from ocean waters.

15 Claims, No Drawings

SEPARATION AND RECOVERY OF IONIC SUBSTANCES BY FLUORINE-CONTAINING COMPOUND

It has been known that certain compounds entrap ionic substances such as metal ions by a phenomenon called coordination or inclusion. As illustrative of such compounds having the ability to include ionic substances, there can be mentioned chelate resins, ion exchange resins, crown ethers, cryptand, and high-molecular-weight counterparts of these. Such compounds are hereinafter referred to as including compounds.

Generally, including compounds denote compounds having the ability to form inclusion compounds by including not only ionic substances but also various other compounds, and those which have the ability to include ionic substances are specifically called ionophores. The inclusion compounds denote intermolecular compounds composed of two components in which one component forms spaces such as channels or cavities and the other component is confined within the spaces.

Since such polymers as chelate resins and ion exchange resins are insoluble in water, it is easy to recover metals entrapped by these resins. In spite of this advantage, these resins generally have the defect of being little selective for metal ions and undergoing configurational change or degradation.

The purpose of increasing the molecular weight of ion entrapping agents of this type is to position ligands, which are to be involved in the interaction of these agents with ionic substances, in a certain fixed space, thereby increasing the concentration of ligands locally. They, however, have the defect that compact spaces for selective catching of metal ions, etc. cannot be secured fully effectively because their primary structure is disordered as, for example, seen in the irregular positioning of the ligands in the main chain, or their secondary structure becomes irregular owing to changes in the conformation of the main or side chains of the polymer.

Cyclic including compounds such as crown ethers or cryptand have been developed mainly with a view to securing selectivity for metallic ions. However, processes for producing these compounds generally comprise many synthesis steps and are industrially disadvantageous. There have also been developed compounds capable of entrapping metal ions with increased efficiency by introducing such including compounds into the side chains of polymers, but these compounds are still unsatisfactory from the standpoint of high selectivity as in the case of the aforesaid high-molecular-weight ion entrapping agents.

The inventor has newly found that a specific fluorine-containing compound containing both fluoroalkyl groups and groups having affinity for ionic substances undergo association in water or most organic solvents owing to the oleophobicity and hydrophobicity of the fluoroalkyl groups to form a poly-molecular associated product, and many ionophilic groups gather to form a site of inclusion of ionic substances.

Thus, according to this invention, there is provided a method for selectively recovering an ionic substance, which comprises adding a fluorine-containing compound represented by the following general formula $$[\{Rf\text{-}(A)_a\text{-}Y\}(X)_b]_n(Z)_c \quad (I)$$

wherein

Rf is a fluoroalkyl group having 3 to 20 carbon atoms,

A is a polyvalent linking group having a valence of at least 2,

Y is a group having a valence of at least 1 and affinity for the ionic substance, X is a group having a valence of at least 1 which does not hinder the interaction of said compound with the ionic substance, Z is a polyvalent linking group having a valence of at least 2 which links at least 2 fluorine-containing compounds, a, b and c are 0 or 1 and are determined independently from each other, and n is an integer of at least 1, to a liquid medium in which the ionic substance is dissolved or dispersed, and separating the ionic substance from the liquid medium by including it in the fluorine-containing compound.

According to this method, the fluorine-containing compound is added, either as such or as a solution in a solvent having a solubility parameter, δ, of at least 7.5, to a liquid medium in which an ionic substance is present. The added fluorine-containing compound is fully contacted with the liquid medium in the state of solid-liquid or liquid-liquid to include the ionic substance in the fluorine-containing compound and thus to separate it from the liquid medium.

Since the ionic substance to be separated differs depending upon the kind of the fluorine-containing compound, the desired ionic substance can be separated effectively by properly selecting the fluorine-containing compound.

Examples of the ionic substance include a variety of cationic substances such as metal ions, metal oxide ions, complex ions, amino acids and ammonium compounds.

The fluorine-containing compound used in the invention can be easily synthesized by a simple method at low cost. Furthermore, since it has high chemical stability, it can withstand repeated use.

The present invention is broadly applicable to a wide range of technical fields in which specified ionic substances are to be separated and recovered from various ionic substances existing in various liquid media such as water and organic solvents, for example to mineral engineering concerned with the recovery of useful mineral resources from sea water; metallurgical technology involving wet-refining a solution of an inorganic acid salt of copper, cobalt or nickel by a liquid-liquid extracting method in place of the electrical refining; water-treatment for cleaning industrial and household waste liquors; the recovery and concentration of radioactive wastes in the atomic power industry; the harvesting of biologically active substances from culture broths resulting from the cultivation of microorganisms in pharmaceutical produciton; and the production of medicines or therapeutic adjuvants for treating diseases by removing unwanted metallic ions from the human body, or the production of metal ion sensers for devices of measuring the ion concentration of blood and other body fluids.

Since the fluorine-containing compound of general formula (I) has extremely low affinity for organic solvents owing to the presence of the fluoroalkyl groups Rf, intramolecular or intermolecular association takes place. As a result, functional groups in Y having affinity for metallic ions approach each other to form a site of inclusion as in the case of cyclic ionophores.

It should be understood that the term "inclusion" as used herein does not mean such a phenomenon as the formation of an organic salt between an anion such as a carboxyl group and a cation such as $Ca^{2+}$.

In order that the association is compact and stable, the group Rf should be a perfluoroalkyl group having at least 3 carbon atoms. It may be linear, branched, or cyclic (e.g., a perfluorocyclohexyl group) in structure, or have a mixture of such structures. Furthermore, one or more oxygen atoms may be introduced into the main chain as in $(CF_3)_2CFOCF_2CF_2$—.

Examples of the polyvalent linking group A in general formula (I) include not only such groups as —O—, —S—, —CO—, —$SO_2$—, —N<, —CON<, and —$SO_2$N<, but also aliphatic groups optionally containing a hetero atom, such as $-(CH_2)_p-$ (where p is an integer of 1 to 5),

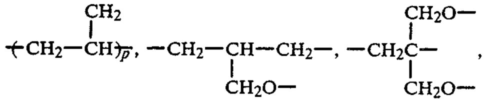

—$CH_2CH_2$N<, —$CH_2CH_2$S—, —$CH_2CH_2SO_2$N<, and —$CH_2CH_2$CON<; and groups containing an aromatic ring, such as

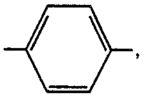, 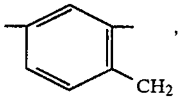, 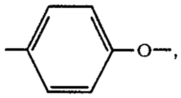,

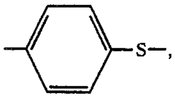, 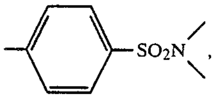,

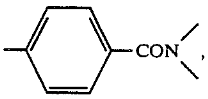, and 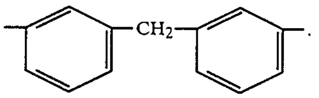.

Examples of the functional groups constituting the group Y having affinity for ionic substances are a sulfonyl group, a sulfonamido group, a carbonyl group, a carbonyl ester group, a urethane linkage group, a urea linkage group, and an ether linkage group.

A certain polyvalent linking group A may be involved in the inclusion of an ionic substance, and in this case A corresponds to part of Y. In this sense, a is 0 or 1.

The group X does not directly participate in the including action, but affects the solubility of the fluorine-containing compound in organic solvents or the structure of the site of inclusion. For example, it includes alkyl groups and aromatic groups. The group X is not essential, and in this sense, b is 0 or 1.

Various groups Z can exist. Examples of preferred groups are

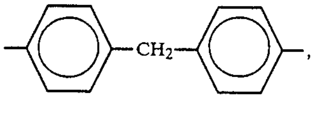, $(CH_2)$—,

-continued

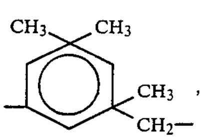, 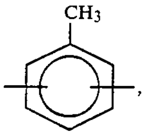,

—$CH_2CH_2O$—$_q CH_2CH_2$— (where q is an integer of 1 to 12),

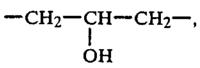, and 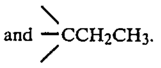.

The fluorine-containing compound in this invention may be without Z, and in this sense, c is 0 or 1. When it has Z (i.e. c is 1), n represents the valence of Z. When the fluorine-containing compound does not have Z (when c is 0), n is 1.

Many specific separating procedures are available for separating ionic substances using the fluorine-containing compound in accordance with this invention as an ionophore. Roughly, they can be grouped in the following three embodiments.

A first embodiment is a method which comprises adding a solid or liquid fluorine-containing compound to an aqueous or organic solvent solution of an ionic substance such as a metal ion, and including the ionic substance in the fluorine-containing compound at a liquid-solid interface or a liquid-liquid interface. This embodiment is practiced, for example, when the solubility of the fluorine-containing compound in water and an organic solvent is extremely low, for example $1\times10^{-4}$ % by weight or below.

A second embodiment is a method which comprises dissolving the fluorine-containing compound in a substantially water-immiscible organic solvent, and contacting the organic solvent solution with an aqueous solution containing an ionic substance dissolved therein. In this embodiment, the fluorine-containing compound desirably has a solubility of not more than $2\times10^{-2}$ % by weight in water and at least $1\times10^{-4}$ % by weight in organic solvents. A liquid-liquid extracting method, and a liquid film method are included in this embodiment.

A third embodiment is a method which comprises dissolving the fluorine-containing compound in an organic solvent solution containing an ionic substance dissolved therein and then recovering the precipitated inclusion compound.

When the fluorine-containing compound is dissolved in an organic solvent, the state of its association varies depending upon the kind of the organic solvent, and its selectivity for ionic substances slightly changes accordingly. Hence, the selectivity can be controlled to some extent according to the properties of the solvent used, and the range of applicability of the fluorine-containing compound as an ionophore is broad.

In order that the properties of the fluorine-containing compound as an ionophore may be fully exhibited, the solvent should generally have a solubility parameter $\delta$ of preferably at least 7.5, especially preferably at least 8.5. Specific examples of such a solvent are chloroform, dichloromethane, dichloroethane, tetrahydrofuran, ethyl acetate and nitromethane.

Ionic substances to be entrapped by the method of this invention include, inorganic metal salts, organic metal salts, amino acids, and quaternary ammonium salts. Metal ions, metal oxide ions, and metal complex ions are suitable ions to be entrapped.

The included ionic substances can be easily recovered by contact with an aqueous solution of hydrochloric acid, sulfuric acid, nitric acid, ammonium carbonate, sodium bicarbonate, sodium carbonate, sodium hydroxide, etc. (eluent), and the fluorine-containing compound can be repeatedly used. For example, in liquid-liquid extraction, the organic layer left after extraction of the ionic substance can be contacted with an eluent to perform back-extraction, and the organic layer can be re-used. Accordingly, the fluorine-containing compound in accordance with this invention is suitable as a carrier for use in a liquid film method in which extraction and recovery can be carried out in a single system.

The present invention can be utilized in the various technical fields exemplified hereinabove. An especially characteristic and typical manner of utilizing the method of this invention is the recovery of useful or hazardous metals from natural water (sea water, mineral water, underground water, river water, lake water, marsh water, etc.), and industrial and household waste waters. Recovery of uranium from sea water, and the separation of rare earth elements from sea water and its concentration and purification are most interesting application. Recovery of a uranyl ion is described below in detail.

Owing to the scarcity of fossile fuels, the utilization of atomic energy as a substitute energy source has recently attracted a great deal of attention. The quantity of uranium as a material for providing atomic energy in the earth's mineral deposits is estimated at about one million tons, which is by no means abundant in view of the anticipated future demand. In contrast, about $45\times10^8$ tons of uranium exists dissolved in the entire ocean waters, and if it can be extracted with good efficiency, sea water will become an inexhaustible source of uranium supply.

Titanic acid, ion exchange resins, and chelate resins are among those materials which are now known as adsorbents for uranium. But none have been found to be commercially feasible and have the ability to adsorb uranium with high selectivity from sea water in which a variety of metal ions exist together.

Recently, macrocyclic hexaketone capable of take up a uranyl ion selectively by inclusion was reported [Tabuse et al., Nature, 280, 665 (1979)]. In the synthesis of such a cyclic compound, however, the number of process steps is generally large, and a special process is necessary. Hence, it is industrially disadvantageous.

The present inventor discovered that a metal ion can be included in a fluorine-containing ionophore obtained on the basis of the new idea described hereinabove by using the properties of a fluoroalkyl group. Since the fluoroalkyl group has very low affinity for organic solvents, the introduction of one or more fluoroalkyl groups into molecules induces association between or within the molecules of the resulting fluorine-containing compound. As a result, functional groups capable of interacting with the metal ion approach each other to form a site of inclusion as in the case of a cyclic ionophore. Accordingly, a fluorine-containing compound obtained by making a specified molecular design can selectively include a uranyl ion and recover uranium in high yields at low cost. Furthermore, such a fluorine-containing compound is very useful in practical application because it can recover a uranyl ion in good yields even from natural ocean waters in which a variety of ions exist together.

The included uranyl ion can be easily recovered by contacting the inclusion compound with an aqueous solution of, for example, hydrochloric acid, nitric acid, sulfuric acid, ammonium carbonate, sodium hydroxide, sodium bicarbonate or sodium carbonate. Moreover, the fluorine-containing compound in accordance with this invention can be repeatedly used with industrial advantage.

Since the fluorine-containing compound in accordance with this invention dissolves in the associated state in many water-immiscible organic solvents, it can be used as an ion carrier of a liquid film by impregnating the solution in a porous polymeric membrane or adding an emulsifying agent to form a (w/o)/w type emulsion (an emulsion obtained by the dispersion of a w/o type emulsion in water). Or it can be supported on a solid support and used as an adsorbent for a uranyl ion.

The fluorine-containing compounds of general formula I in accordance with this invention will be specifically described. Some of these compounds may be represented by the following general formulae II, III and IV.

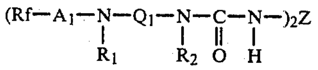
(II)

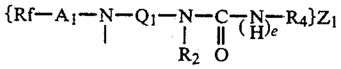
(III)

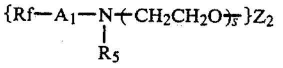
(IV)

In the above formulae:

Rf is a fluoroalkyl group having 3 to 16 carbon atoms;

$A_1$ is a divalent linking group corresponding to A in general formula I;

$R_1$ is a hydrogen atom, an alkyl group having 1 to 12 carbon atoms, a methoxyethyl group, an ethoxyethyl group,

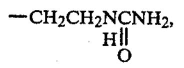

or $-(CH_2CH_2O)_r H$ where r is an integer of 1 to 5;

$R_2$ is a hydrogen atom, or an alkyl or hydroxyalkyl group having 1 to 3 carbon atoms;

$Q_1$ is $-(CH_2)_l-$ (where l is an integer of 2 to 6), $-(CH_2)_l O(CH_2)_m-$ (l and m are integers of 2 to 6), or

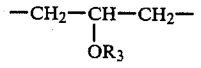

-continued (where $R_3$ is a hydrogen atom or an alkyl group having 1 to 3 carbon atoms);

$R_4$ is an alkyl or alkenyl group having 1 to 6 carbon atoms, an alkyl group having 1 to 6 carbon atoms and 1 or 2 etheric oxygen atoms, or an aromatic group including a ring-substituted aromatic group;

$R_5$ is a hydrogen atom, an alkyl, hydroxyalkyl or alkenyl group having 1 to 16 carbon atoms, an alkyl group having 1 to 16 carbon atoms and 1 to 2 etheric oxygen atoms, an aromatic group, or a group containing an aromatic ring;

Z is a divalent linking group corresponding to Z in general formula I;

$Z_1$ is $-CH_2CH_2O-)_fCH_2CH_2-$ (where f is an integer of 1 to 8), or

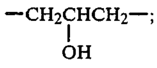

and $Z_2$ is $-CH_2CH_2OCH_2CH_2-$.

These fluorine-containing compounds of general formulae II, III and IV have been unknown heretofore.

The ability of these fluorine-containing compounds to include ionic substances and their selectivity for ionic substances vary from compound to compound. The degrees of their including abilities and their selectivities for ionic substances cannot be fully anticipated from their chemical structures, and where it is desired to know these factors accurately, an experimental work is required.

Since, however, fluorine-containing compounds of general formula IV can include ionic substances by their very thin membrane, they can also be used as accelerators for ionic reactions of inorganic salts with organic compounds, i.e. organic ionic reactions. The action of these fluorine-containing compounds is directly a kind of catalytic activity for accelerating the reaction by moving the ionic substance from an inorganic phase (or aqueous phase) to an organic phase, but their essential nature is to trap and separate the ionic substance. Accordingly, the use of the fluorine-containing compounds in this way is one embodiment of the present invention.

Table 1 gives typical examples of the fluorine-containing compounds in accordance with this invention.

In Table 1, letters A to N represent the following chemical structures of fluoroalkyl-containing compounds.

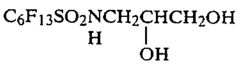
A

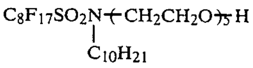
B

-continued

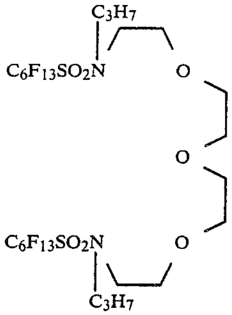
C

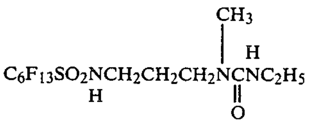
D

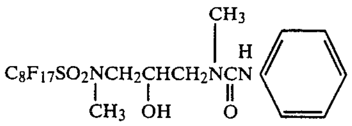
E

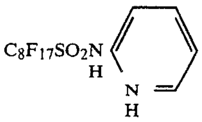
F

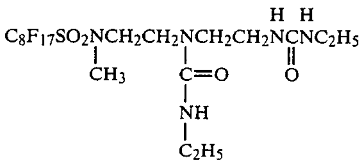
G

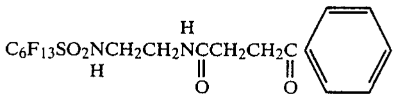
H

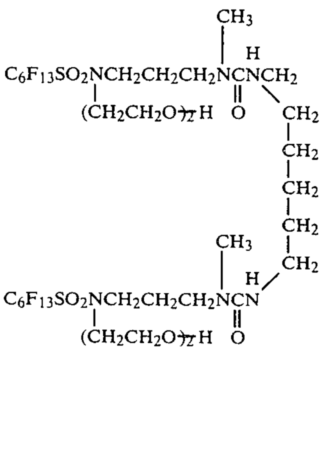
I

-continued
J
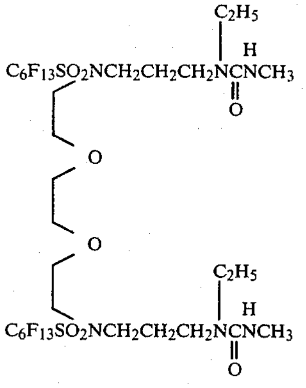
K
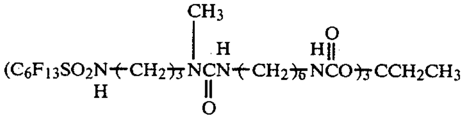
-continued
L
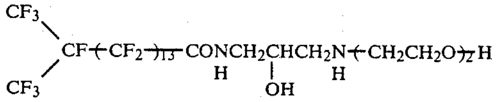
M
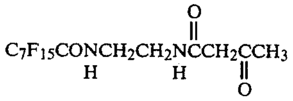
N
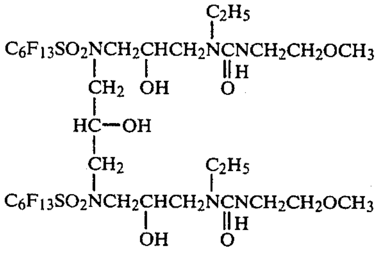
TABLE 1
| Fluoroalkyl-containing compound | Rf | A | Y | X |
|---|---|---|---|---|
| A | $C_6F_{13}-$ | 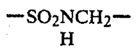 | 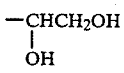 | — |
| B | $C_8F_{17}-$ | 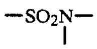 | $-(CH_2CH_2O)_5H$ | $-C_{10}H_{21}$ |
| C | $C_6F_{13}-$ | 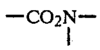 | $-CH_2CH_2O-$ | $-C_3H_7$ |
| D | $C_6F_{13}-$ | 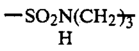 | 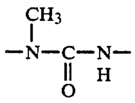 | $-C_2H_5$ |
| E | $C_8F_{17}-$ | 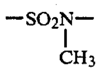 | 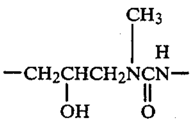 | 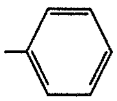 |
| F | $C_8F_{17}-$ | 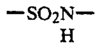 | 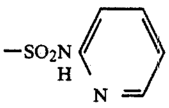 | — |
| G | $C_8F_{17}-$ | 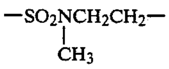 | 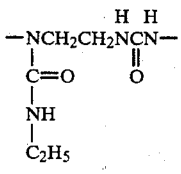 | $-C_2H_5$ |
| H | $C_6F_{13}-$ | 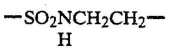 | 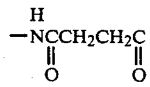 | 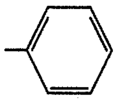 |

TABLE 1-continued

| | | | | |
|---|---|---|---|---|
| I | $C_6F_{13}-$ | 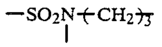 | 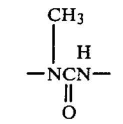 | $-(CH_2CH_2O)_2H$ |
| J | $C_6F_{13}-$ | 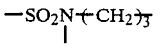 | 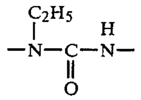 | $-CH_3$ |
| K | $C_6F_{13}-$ | 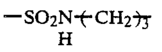 | 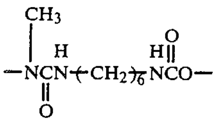 | — |
| L | 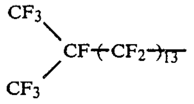 | 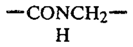 | 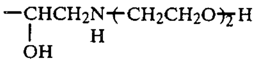 | — |
| M | $C_7F_{15}-$ | 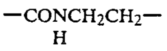 | 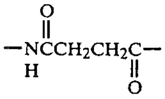 | $-CH_3$ |
| N | $C_6F_{13}-$ | 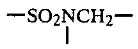 | 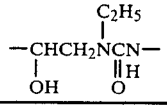 | $-CH_2CH_2OCH_3$ |

| Fluoroalkyl-containing compound | Z | n | a | b | c |
|---|---|---|---|---|---|
| A | — | 1 | 1 | 0 | 0 |
| B | — | 1 | 1 | 1 | 0 |
| C | 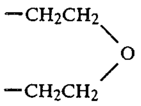 | 2 | 1 | 1 | 1 |
| D | — | 1 | 1 | 1 | 0 |
| E | — | 1 | 1 | 1 | 0 |
| F | — | 1 | 0 | 0 | 0 |
| G | — | 1 | 1 | 1 | 0 |
| H | — | 1 | 1 | 1 | 0 |
| I | $-(CH_2)_6-$ | 2 | 1 | 1 | 1 |
| J | $-(CH_2CH_2O)_2CH_2CH_2-$ | 2 | 1 | 1 | 1 |
| K | 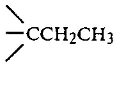 | 3 | 1 | 0 | 1 |
| L | — | 1 | 1 | 1 | 0 |
| M | — | 1 | 1 | 1 | 0 |
| N | 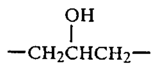 | 2 | 1 | 1 | 1 |

In addition to those exemplified in Table 1, there are many other fluorine-containing compounds in accordance with this invention, and they are described in Examples given hereinbelow. Analysis of these other compounds in accordance with Table 1 shows that they have chemical structures corresponding to general formula I. The properties of these fluorine-containing compounds are shown in Examples given hereinbelow.

Since, those compounds of the invention which are represented by general formulae II, III and IV are novel compounds, processes for manufacturing them will be described briefly below.

Most of the compounds of general formula II can be produced in high yields by a process which comprises reacting a reactive polyfluoroalkylsulfonic acid, a polyfluoroalkylcarboxylic acid or an acid halide or ester of such an acid, all of which are easily obtainable in general, with a diamine of the general formula $$H_2N-Q_1-N(R_2)H$$

wherein $Q_1$ is $-(CH_2)_l-$ where l is an integer of 2 to 6, $-(CH_2)_l-O-(CH_2)_m-$ where l and m are integers of 2 to 6, or $$-CH_2\underset{\displaystyle OH}{\underset{|}{C}}HCH_2-;$$

where $R_3$ represents an alkyl group having 1 to 3 carbon atoms, and $R_2$ is an alkyl or hydroxyalkyl group having 1 to 3 carbon atoms or a hydrogen atom, to form a fluorine-containing amine compound of the following general formula V $$Rf-A_1-\underset{\displaystyle H}{\underset{|}{N}}-Q_1-\underset{\displaystyle R_2}{\underset{|}{N}}H \qquad (V)$$

wherein

Rf is a polyfluoroalkyl group having 3 to 16 carbon atoms, $A_1$ is a divalent linking group, and $Q_1$ and $R_2$ are as defined above, then reacting the fluorine-containing amine compound with a diisocyanate represented by the following general formula VI $$O{=}C{=}N-Z-N{=}C{=}O \qquad VI$$

wherein

Z is a divalent linking group represented by 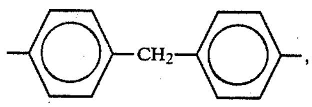, $-(CH_2)_6-$,

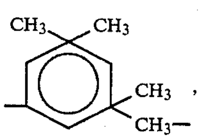, or 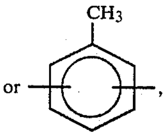, in an aprotic solvent to form a compound represented by the general formula VII $$(R_5-A_1-\underset{\displaystyle H}{N}-Q_1-\underset{\displaystyle R_2}{\underset{|}{N}}-\underset{\displaystyle O}{\underset{\|}{C}}-\underset{\displaystyle H}{\underset{|}{N}}-)_2Z \qquad VII$$

wherein

Rf, $A_1$, $Q_1$, $R_2$ and Z are as defined above, and then reacting the resulting compound with a compound of the general formula $$XR_1$$

wherein

X is a halogen atom, and $R_1$ is an alkyl group having 1 to 12 carbon atoms, a methoxyethyl group, an ethoxyethyl group, a group of the formula $$-CH_2CH_2\underset{\displaystyle H}{\underset{|}{N}}\overset{\displaystyle O}{\overset{\|}{C}}NH_2,$$

or a group of the formula $-(CH_2CH_2O)_nH$ where n is an integer of 1 to 5, in the presence of an alkaline catalyst.

The compound of general formula VII is a kind of the compound of general formula II.

In reacting the compound of general formula V with the diisocyanate of general formula VI, they are stirred in an aprotic solvent such as tetrahydrofuran or benzene usually at a temperature of 0° to 60° C. for 1 to 5 hours.

In the reaction of the fluorine-containing compound of general formula VII with the halogen compound of general formula $XR_1$, the solvent used may include, for example, methyl Cellosolve, ethyl Cellosolve, butyl Cellosolve, butyl carbitol, dimethylformamide, and dimethyl sulfoxide. The suitable reaction temperature is 80° to 140° C., and the suitable reaction time is 5 to 16 hours. The metal halide or halogenated amine salt as by-products may sometimes precipitate as crystals at room temperature. In many cases, however, such by-products are included in the resultant fluorine-containing compound and dissolved uniformly. In such a case, the reaction product can be purified by distilling off the solvent under reduced pressure at a temperature of not more than 140° C., dissolving the residue in an alcoholic solvent such as ethanol, and removing the salts by a cation exchange resin.

The fluorine-containing compounds of general formula III in accordance with this invention can be produced in high yields by a process which comprises replacing the N—H proton of $$-A_1-\underset{\displaystyle H}{\underset{|}{N}}-Q_1-$$

of a fluorine-containing compound having a urea linkage group or a carbonamide group in the molecule represented by the general formula $$Rf-A_1-\underset{\displaystyle H}{\underset{|}{N}}-Q_1-\underset{\displaystyle R_2}{\underset{|}{N}}-\overset{\displaystyle O}{\overset{\|}{C}}-\left(\overset{\displaystyle H}{N}\right)_a-R_4 \qquad VIII$$

wherein $A_1$, $Q_1$ and $R_2$ are as defined above, $R_4$ is an alkyl or alkenyl group having 1 to 6 carbon atoms, an alkyl group having 1 to 6 carbon atoms and 1 or 2 etheric oxygen atoms, or an aromatic group including a ring-substituted aromatic group, and a is an integer of 0 or 1, by Na or K using $CH_3ONa$, NaH or $(CH_3)_3COK$, and reacting the resulting product with a dihalogenated oligoethylene glycol or dihalogenated isopropyl alcohol represented by the general formula $$X-(CH_2CH_2O)_j-CH_2CH_2-X \quad . \quad . \quad . \qquad IX$$

or $$X-CH_2\underset{\displaystyle OH}{\underset{|}{C}}HCH_2-X \quad \ldots \quad X$$

wherein

X represents a halogen atom, and f is an integer of 1 to 8.

The reaction is carried out in a solvent such as methyl Cellosolve, ethyl Cellosolve, butyl Cellosolve, butyl carbitol, dimethylformide or dimethyl sulfoxide. The suitable reaction temperature is 80° to 140° C., and the suitable reaction time is 5 to 16 hours. Sometimes, the metal halide or halogenated amine salt as a by-product may be precipitated as crystals at room temperature, or included in the resulting fluorine-containing compound in the uniformly dissolved state. In the latter case, the reaction product can be purified by distilling off the solvent under reduced pressure at a temperature of not more than 140° C. dissolving the residue in an alcohol solvent such as ethanol, and removing the salts by a cation exchange resin.

The fluorine-containing compound of general formula VIII used as a starting material in the above reaction can be produced in good yields by reacting a fluorine-containing compound of general formula XI $$Rf-A_1-\underset{H}{N}-Q_1-\overset{R_2}{\overset{|}{N}}H \qquad XI$$

wherein

Rf, A, $Q_1$ and $R_2$ are as defined above, which is obtained by reacting an easily available polyfluoroalkylsulfonic acid, polyfluoroalkyl carboxylic acid or its acid halide or ester with a diamine of the general formula $$H_2N-Q_1-\overset{R_2}{\overset{|}{N}}H$$

wherein $Q_1$ and $R_1$ are as defined, with an isocyanate of the general formula $$R_4-N=C=O$$

wherein $R_4$ is as defined above, in an aprotic solvent; or reacting the fluorine-containing compound of general formula XI with an acid anhydride of the general formula $$R_4-\overset{O}{\overset{\|}{C}}-O-\overset{O}{\overset{\|}{C}}-R_4 \qquad /$$

wherein $R_4$ is as defined, in the absence of catalyst or in the presence of a basic catalyst such as pyridine.

Compounds of general formula IX in which f is 1 and 2 can be purchased at low cost, and those of general formula IX in which f is 3 or more can be easily synthesized in accordance with the method described in C. J. Pedersen, J. Amer. Chem. Soc., 89, 7017 (1967).

The fluorine-containing compounds of general formula IV can be produced in high yields by two processes.

One process comprises replacing the N—H proton of a fluorine-containing compound of general formula XII $$Rf-A_1-\overset{H}{N}R_5 \qquad XII$$

wherein

Rf and $A_1$ are as defined, and $R_5$ represents a hydrogen atom, an alkyl, hydroxyalkyl or alkenyl group having 1 to 16 carbon atoms, an alkyl group having 1 to 16 carbon atoms and 1 or 2 etheric oxygen atoms, an aromatic group, or a group containing an aromatic ring, by Na or K using $CH_3ONa$, NaH or $(CH_3)_3COK$, and then reacting the product with a dihalogenated oligoethylene glycol of the general formula $$X\text{-}(CH_2CH_2O)_g CH_2CH_2-X \quad \ldots\ldots \quad XIII$$

wherein

X is a halogen atom, and g is an integer of 1 to 12, in the same way as in the production of the compounds of general formula III.

Each of the compounds of general formulae XII and XIII needs not to be a single compound.

The fluorine-containing compound of general formula XII used as a starting material in the above reaction can be produced in good yields by reacting an easily available reactive polyfluoroalkylsulfonic acid, fluoroalkylcarboxylic acid or its acid halide or ester with a primary amine of the general formula $R_5NH_2$ where $R_5$ is as defined.

The other process comprises reacting a compound of the general formula $$Rf-A_1-\overset{R_5}{\overset{|}{N}}CH_2CH_2OH \quad \ldots\ldots \quad XIV$$

wherein

Rf, $A_1$ and $R_5$ are as defined, with a compound of the general formula $$TsO\text{-}(CH_2CH_2O)_i CH_2CH_2OTs \quad \ldots \quad XV$$

wherein

Ts is a tosyl group, and i is an integer of 1 to 11, in the presence of an alkaline catalyst.

In this case, too, the compound of general formula XIV needs not to be a single compound.

The reactions of above two processes are carried out in the presence of a solvent such as dimethoxyethane, tetrahydrofuran, dimethylformamide and dimethyl sulfoxide. The suitable reaction temperature is 60° to 120° C., and the suitable reaction time is 5 to 15 hours. KOH and NaOH are suitable as the alkaline catalyst because they are inexpensive. NaH is another suitable alkaline catalyst for use in this process. The purification of the product may be effected as in the first-mentioned process for producing the compounds of general formula III.

The compound of general formula XIV used as a starting material in the above reaction can be produced in good yields by reacting the fluorine-containing compound of general formula XII with ethylene chlorohydrin in the presence of an alkaline catalyst. The compound of general formula XV can be produced in good yields by reacting a corresponding oligo ethylene oxide with p-toluenesulfonyl chloride in pyridine.

The following examples illustrate the present invention more specifically. It should be understood that the invention is in no way limited to these specific examples.

EXAMPLE 1

Synthesis of the following compound:

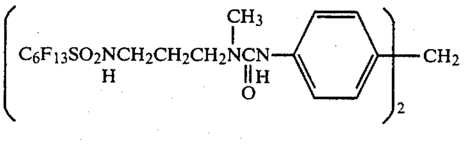

(i) Synthesis of 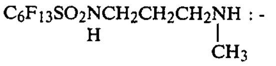 : -

In an atmosphere of nitrogen, 264 g (3.0 moles) of N-methyl-1,3-diaminopropane and 400 g of sufficiently dehydrated isopropyl ether were weighed into a 2-liter three-necked round-bottomed flask equipped with a cooling condenser and a stirrer. With thorough stirring, 422 g (1.05 moles) of perfluorohexylsulfonyl fluoride was added dropwise at room temperature. The mixture was stirred at 50° C. for 3 hours, and then the isopropyl ether was removed under reduced pressure. The yellow solid residue was dissolved in 500 ml of ethanol, and the solution was gradually poured into 8 liters of distilled water with stirring to age the crystals. The supernatant liquid was removed by decantation, and the residue was further decanted three times using 5 liters of distilled water each time. The crystals were collected by filtration, and water was fully removed. The crystals were then washed with 1 liter of ethyl acetate, and dried under reduced pressure at 70° C. to give 440 g of slightly yellow crystals.

Melting point: 171.0°-172.0° C.

| Elemental analysis (%): | C | H | N |
|---|---|---|---|
| Found: | 25.5 | 2.4 | 6.0 |
| Calculated: | 25.5 | 2.3 | 6.0 |

IR spectrum: 1370 $cm^{-1}$ (—$SO_2N$<, ν as).

NMR spectrum ($CD_3OD$ solvent, TMS standard): 1.80 ppm (m, 2H), 2.65 ppm (s, 3H), 3.05 ppm (t, 2H), 3.26 ppm (t, 2H).

(ii) Synthesis of 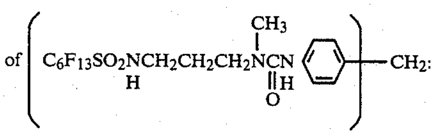 : -

In an atmosphere of nitrogen, 50 g (0.106 mole) of N-(3-methylaminopropyl)perfluorohexylsulfonamide and 300 ml of fully dehydrated tetrahydrofuran were weighed into a 500 ml three-necked roung-bottomed flask equipped with a dry silica gel tube and a stirrer, and were stirred at room temperature to form a solution. With vigorous stirring at room temperature, 13.9 g (0.055 mole) of 4,4'-diphenylmethane diisocyanate was gradually added, and the mixture was stirred at room temperature for 3 hours. The tetrahydrofuran was distilled off under reduced pressure to give 63 g of a slightly yellow solid.

Melting point: 84.0° C.

| Elemental analysis (%): | C | H | N |
|---|---|---|---|
| Found: | 36.5 | 2.6 | 7.0 |
| Calculated: | 35.3 | 2.7 | 7.1 |

IR spectrum: 1370 $cm^{-1}$ (—$SO_2N$<, ν as), 1645 $cm^{-1}$ (>N—CO—NH—).

NMR spectrum ($CD_3COCD_3$ solvent, TMS standard): 1.85 ppm (m, 4H), 3.03 ppm (s, 6H), 3.04 ppm (t, 4H), 3.61 ppm (t, 4H), 3.82 ppm (s, 2H), 7.20 ppm (q, 8H).

EXAMPLE 2

Synthesis of the following compound:

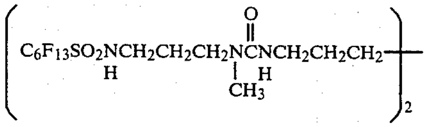

In an atomosphere of nitrogen, 75 g (0.16 mole) of N-(3-methylaminopropyl)perfluorohexyl sulfonamide and 400 ml of fully dehydrated tetrahydrofuran were weighed into a 1-liter three-necked round-bottomed flask equipped with a dry silica gel tube and a stirrer, and stirred at room temperature to form a solution. With vigorous stirring at room temperature, 14.4 g (0.084 mole) of hexamethylene diisocyanate was added gradually to the solution. The mixture was stirred at room temperature for 3 hours, and the tetrahydrofuran was distilled off under reduced pressure to give 89 g of a slightly yellow oil.

| Elemental analysis (%): | C | H | N |
|---|---|---|---|
| Found: | 31.1 | 3.0 | 7.7 |
| Calculated: | 30.3 | 3.1 | 7.6 |

IR spectrum: 1370 $cm^{-1}$ (—$SO_2N$<, ν as), 1645 $cm^{-1}$ (>N—CO—NH—).

NMR spectrum ($CD_3COCD_3$ solvent, TMS standard): 1.32 ppm (m, 8H), 1.78 ppm (m, 4H), 2.89 ppm (s, 6H), 3.21 ppm (m, 8H), 3.60 ppm (t, 4H).

EXAMPLE 3

Synthesis of the following compound:

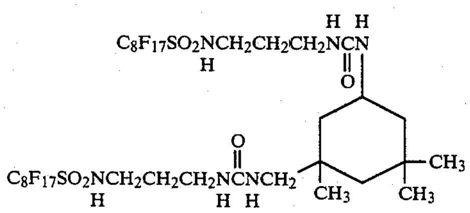

In an atmosphere of nitrogen, 11.7 g (0.021 mole) of N-(3-aminopropyl)perfluorooctylsulfonamide and 100 ml of fully dehydrated tetrahydrofuran were weighed into a 200 ml three-necked round-bottomed flask equipped with a dry silica gel tube and a stirrer, and stirred at room temperature to form a solution. With vigorous stirring at room temperature, 2.8 g (0.0126 mole) of isophorone was gradually added to the solution, and the mixture was stirred at room temperature for 3 hours. By distilling off the tetrahydrofuran under reduced pressure, 14.1 g of a white solid was obtained.

Melting point: 112° to 113° C.

| Elemental analysis (%): | C | H | N |
|---|---|---|---|
| Found: | 30.8 | 2.4 | 6.3 |
| Calculated: | 30.6 | 2.6 | 6.3 |

IR spectrum: 1370 $cm^{-1}$ ($—SO_2N<$, ν as), 1650 $cm^{-1}$ (—NH—CO—NH—). An absorption of —N=C=O (2250 $cm^{-1}$) was not observed at all.

Ninhydrin color reaction: negative.

EXAMPLE 4

Synthesis of the following compound:

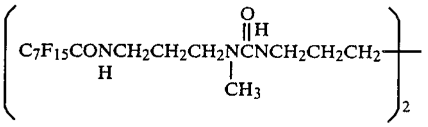

In an atmosphere of nitrogen, 38.7 g (0.08 mole) of N-(3-methylaminopropyl)perfluoroheptylcarbonamide and 250 ml of fully dehydrated tetrahydrofuran were weighed into a 400 ml three-necked round-bottomed flask equipped with a dry silica gel tube and a stirrer, and stirred at room temperature to form a solution. With vigorous stirring at room temperature, 7.2 g (0.042 mole) of hexamethylene diisocyanate was gradually added to the solution, and the mixture was stirred at room temperature for 3 hours. By distilling off the tetrahydrofuran under reduced pressure, 45.9 g of a colorless clear oil was obtained.

| Elemental analysis (%): | C | H | N |
|---|---|---|---|
| Found: | 34.0 | 3.0 | 7.6 |
| Calculated: | 33.8 | 3.0 | 7.4 |

IR spectrum: 1640-1650 $cm^{-1}$ (—CON<, >N—CO—NH—). An absorption of —N=C=O (2250 $cm^{-1}$) was not observed at all.

NMR spectrum ($CD_3COCD_3$ solvent, TMS standard): 1.33 ppm (m, 8H), 1.80 ppm (m, 4H), 2.26 ppm (t, 4H), 2.89 ppm (s, 6H), 3.21 ppm (m, 8H).

EXAMPLES 5 TO 15

Table 2 summarizes the structural formulae and melting points of the compounds of this invention prepared in the same way as in Examples 1, 2, 3, and 4 from known starting materials.

TABLE 2

| Example No. | Structural formula | Melting point (°C.) |
|---|---|---|
| 5 | 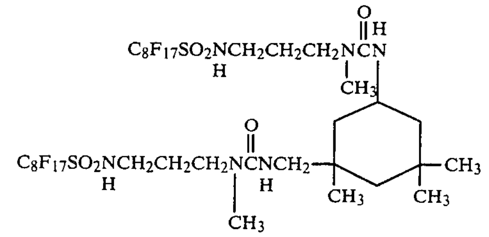 | 98-99 |
| 6 | 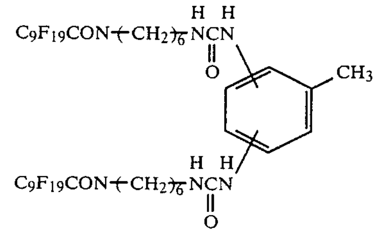 | 121-123 |
| 7 | 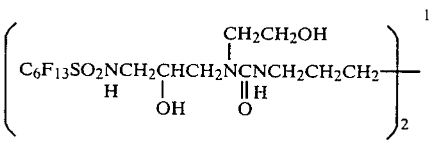 | Paste[2] |
| 8 | 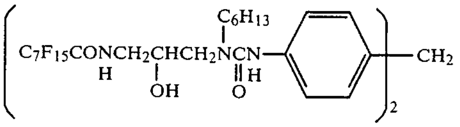 | 39-40 |

TABLE 2-continued
| | | | |
|---|---|---|---|
| 9 | 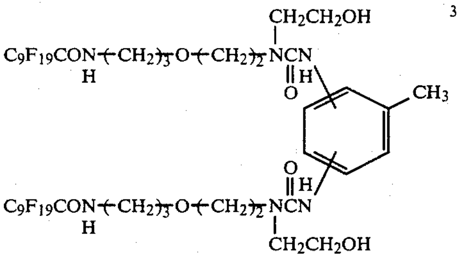 | 3 | Paste[4] |
| 10 | 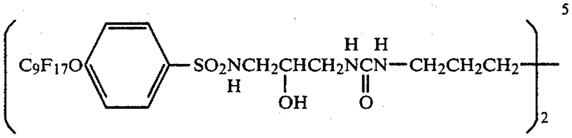 | 5 | 55–56 |
| 11 | 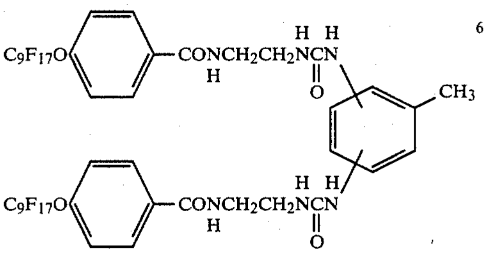 | 6 | 72–76 |
| 12 | 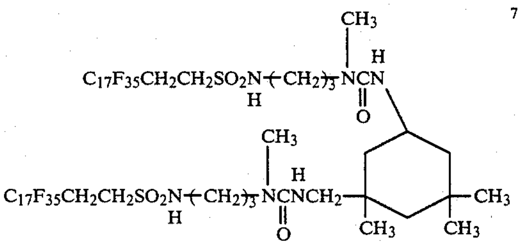 | 7 | 103–106 |
| 13 | 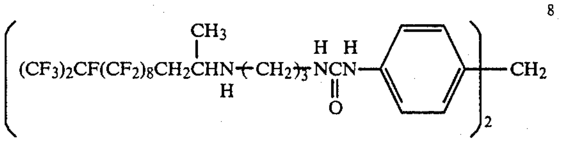 | 8 | 63–65 |
| 14 | 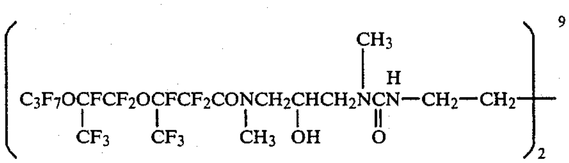 | 9 | Paste[10] |
| 15 | 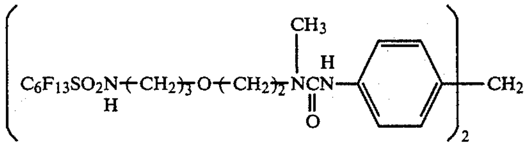 | | Paste[11] |
Note
[1]Synthesized from
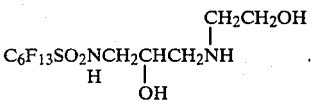
[2]Elemental analysis (%):
Found: C, 30.2; H, 2.9; N, 7.0,
Calcd.: C, 30.1; H, 3.0; N, 7.0.
[3]Synthesized from TABLE 2-continued

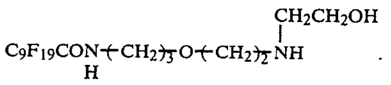

[4]Elemental analysis (%):
Found: C, 34.7; H, 2.8; N, 5.5,
Calcd.: C, 34.6; H, 2.6; N, 5.6.

[5]Synthesized from

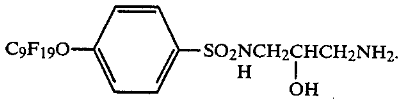

[6]Synthesized from

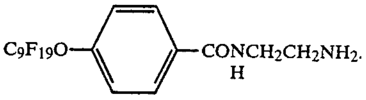

[7]Synthesized from

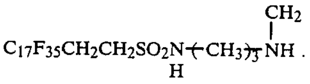

[8]Synthesized from

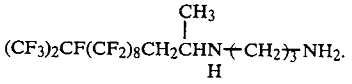

[9]Synthesized from

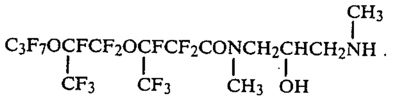

[10]Elemental analysis (%):
Found: C, 30.0; H, 2.3; N, 5.8,
Calcd.: C, 30.2; H, 2.4; N, 5.9.

[11]Elemental analysis (%):
Found: C, 36.6; H, 2.9; N, 6.6,
Calcd.: C, 36.6; H, 3.1; N, 6.6.

EXAMPLE 16

Synthesis of the following compound:

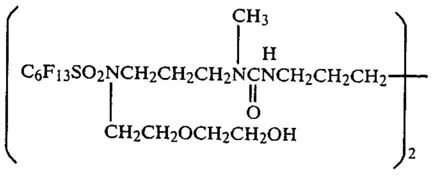

Into a 200 ml three-necked round-bottomed flask equipped with a cooling condenser and a stirrer were weighed 10 g (0.093 mole) of the compound shown in Example 2,

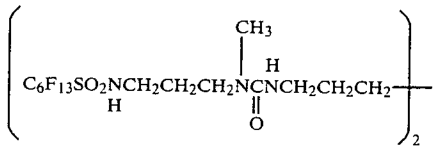

and 80 g of fully dehydrated methyl Cellosolve, and they were heated to form a solution. At 80° C., 4.3 g (0.022 mole) of a 38% methanol solution of sodium methylate was added dropwise to the solution, and the mixture was heated to 110° C. to distill off methanol. Then, 2.4 g (0.022 mole) of β-chloroethoxyethanol was added gradually. The reaction was carried out at 90° C. for 8 hours, and then, the methyl Cellosolve was distilled off under reduced pressure. The oily residue was dissolved in 100 ml of ethanol, and 10 g of Amberlite CG-400 Type-1 was added. The mixture was stirred at room temperature for 1 hour. The ion exchange resin was separated by filtration, and ethanol was distilled off under reduced pressure to give 9.8 g of a slightly yellow paste.

| Elemental analysis (%): | C | H | N |
|---|---|---|---|
| Found: | 33.6 | 3.7 | 6.5 |
| Calculated: | 33.7 | 3.7 | 6.6 |

IR spectrum: 1370 $cm^{-1}$ ($-SO_2N<$, $\nu$ as), 1645 $cm^{-1}$ ($>N-SO-NH-$).

NMR spectrum ($CD_3OD$ solvent, TMS standard): 1.35 ppm (m, 8H), 1.79 ppm (m, 4H), 2.87 ppm (s, 6H), 3.20 ppm (m, 8H), 3.70 ppm (m, 20H), 4.12 ppm (t. 1H).

EXAMPLE 17

Synthesis of the following compound:

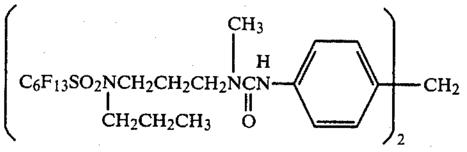

Into a 200 ml three-necked round-bottomed flask equipped with a cooling condenser and a stirrer were weighed 5 g (0.0043 mole) of the compound shown in Example 1,

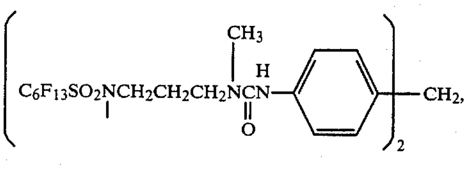

and 70 g of fully dehydrated methyl Cellosolve, and dissolved under heat. At 80° C., 1.7 g (0.01 mole) of a 28% methanol solution of sodium methylate was added dropwise, and the mixture was heated to 110° C. to distill off methanol. Then, 1.75 g (0.01 mole) of n-propyl iodide was gradually added, and the reaction was carried out at 90° C. for 8 hours. Then, the methyl Cellosolve was distilled off under reduced pressure. The residue was dissolved in 100 ml of chloroform, and washed with 50 ml of 5N HCl and then 50 ml of pure water. The chloroform layer was dried by molecular sieves for one day, and the chloroform was removed under reduced pressure to give 5.3 g of a yellow paste.

| Elemental analysis (%): | C | H | N |
|---|---|---|---|
| Found: | 38.1 | 3.3 | 6.6 |
| Calculated: | 38.6 | 3.5 | 6.6 |

IR spectrum: 1370 $cm^{-1}$ ($-SO_2N<$, $\nu$ as), 1645 $cm^{-1}$ ($>N-CO-NH-$).

NMR spectrum ($CDCl_3$ solvent, TMS standard): 0.99 ppm (t, 6H), 1.80 ppm (m, 8H), 3.03 ppm (s, 6H), 3.35 ppm (t, 4H), 3.60 ppm (m, 8H), 3.85 ppm (s, 2H), 7.19 ppm (q, 8H).

EXAMPLES 18 TO 24

Table 3 summarizes the structural formulae and melting points of the compounds of this invention synthesized in the same way as in Examples 16 and 17.

TABLE 3

| Example No. | Stuctural formula | Melting point (°C.) |
|---|---|---|
| 18 | 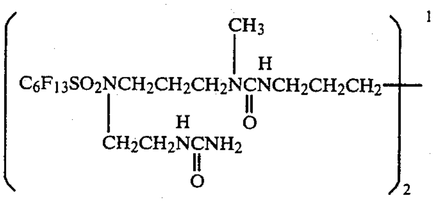 1 | Paste[2] |
| 19 | 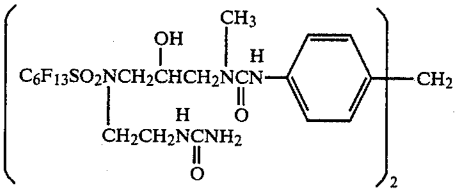 | 41–42 |
| 20 | 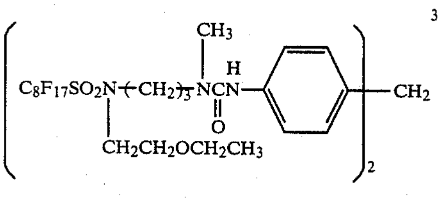 3 | Paste[4] |

TABLE 3-continued

| | | |
|---|---|---|
| 21 | 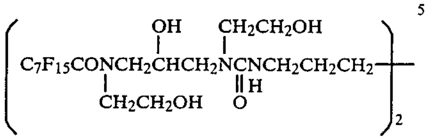 | Paste[6] |
| 22 | 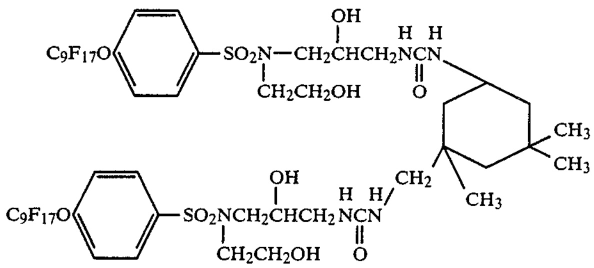 | 54–56 |
| 23 | 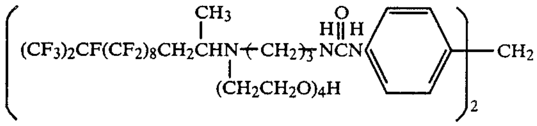 | Paste[7] |
| 24 | 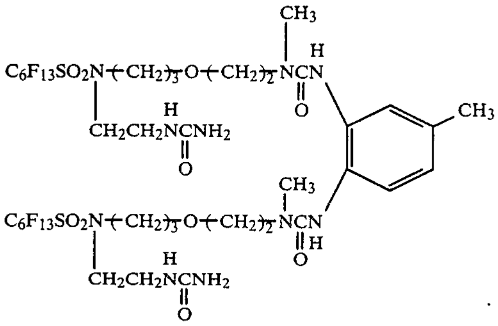 | Paste[8] |

Note

[1]Synthesized from 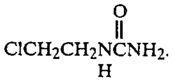

[2]Elemental analysis (%):
Found: C, 33.1; H, 3.5; N, 7.0
Calcd.: C, 33.3; H, 3.8; N, 6.9

[3]Synthesized from $ClCH_2CH_2OCH_2CH_2$.

[4]Elemental analysis (%):
Found: C, 36.6; H, 3.3; N, 5.7
Calcd.: C, 36.8; H, 3.1; N, 5.5

[5]Synthesized from $BrCH_2CH_2OH$.

[6]Elemental analysis (%):
Found: C, 35.0; H, 3.5; N, 6.2
Calcd.: C, 34.7; H, 3.5; N, 6.4

[7]Elemental analysis (%):
Found: C, 42.9; H, 4.2; N, 4.3
Calcd.: C, 43.1; H, 4.0; N, 4.6

[8]Elemental analysis (%):
Found: C, 32.8; H, 3.6; N, 10.5
Calcd.: C, 32.8; H, 3.7; N, 10.4

EXAMPLE 25

Synthesis of the following compound:

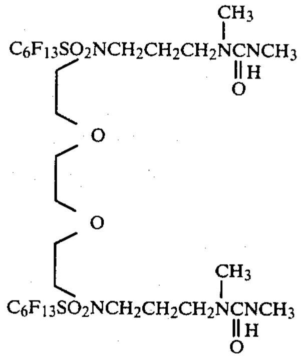

(i) Synthesis 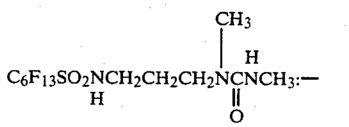:—

In an atmosphere of nitrogen, 47. g (0.1 mole) of N-(3-methylaminopropyl)perfluorohexylsulfonamide and 250 ml of fully dehydrated tetrahydrofuran were weighed into a 500 ml three-necked round-bottomed flask equipped with a dry silica gel tube and a stirrer, and stirred at room temperature to form a solution. With vigorous stirring at room temperature, 20 ml of a tetrahydrofuran solution containing 6.0 g (0.105 mole) of methyl isocyanate was added dropwise. After the addition, the mixture was stirred at room temperature for 3 hours. By distilling off the tetrahydrofuran under reduced pressure, 53 g of a slightly yellow solid was obtained. The product obtained by the above procedure usually has a purity sufficient for use in the subsequent reaction. If required, it may be recrystallized from chloroform-n-hexane.

Melting point: 59.5° to 60.5° C.

| Elemental analysis (%): | C | H | N |
|---|---|---|---|
| Found: | 27.2 | 8.0 | 2.7 |
| Calculated: | 27.3 | 7.9 | 2.6 |

IR spectrum: 1370 $cm^{-1}$ ($—SO_2N<$, $\nu$ as), 1645 $cm^{-1}$ ($>N—CO—NH—$).

NMR spectrum ($CD_3COCD_3$ solution, TMS standard): 1.80 ppm (t, 2H), 2.69 ppm (s, 3H), 2.90 ppm (s, 3H), 3.21 ppm (t, 2H), 3.47 ppm (t, 2H).

(ii) Synthesis of the following compound:

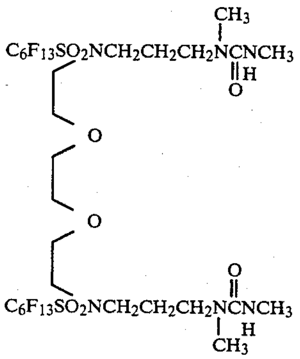

Into a 100 ml three-necked round-bottomed flask equipped with a cooling condenser and a stirrer, 10 g (0.019 mole) of N-[3-(1,3-dimethylureido)propyl)]perfluorohexyl sulfonamide and 70 g of fully dehydrated methyl Cellosolve were weighed, and heated to form a solution. At 80° C., 3.7 g (0.019 mole) of a 28% methanol solution of sodium methylate was added dropwise to the solution, and the mixture was heated to 110° C. to remove methanol. Then, 1.8 g (0.0095 mole) of 1,2-bis(2-chloroethoxy)ethane was gradually added, and the reaction was carried out at 90° C. for 8 hours. The methyl Cellosolve was distilled off under reduced pressure. The paste-like residue was dissolved in 100 ml of ethanol, and 10 g of Amberlite CG-400 (an anion exchange resin made by Rohm & Haas Co.) was added. The mixture was stirred at room temperature for 1 hour. The ion exchange resin was separated by filtration, and ethanol was distilled off under reduced pressure to give 10.5 g of a slightly yellow paste.

| Elemental analysis (%): | C | H | N |
|---|---|---|---|
| Found: | 31.0 | 3.5 | 7.1 |
| Calculated: | 30.8 | 3.3 | 7.2 |

NMR spectrum ($CD_3OD$ solvent, TMS standard): 1.70 ppm (m, 4H), 2.70 ppm (s, 6H), 2.83 ppm (s, 6H), 3.25 ppm (m, 12H), 3.61 ppm (m, 8H).

EXAMPLE 26

Synthesis of the following compound:

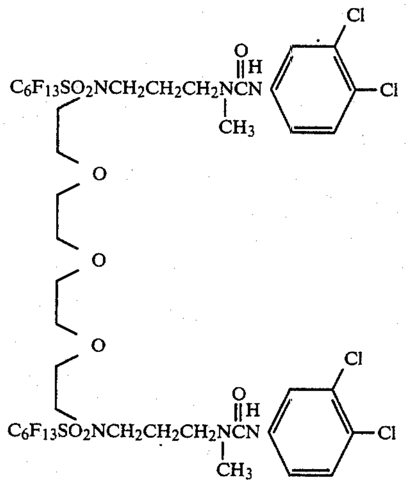

Ten grams (0.0155 mole) of N-{3-[1-methyl-3-(3,4-dichlorophenyl)]propyl}perfluorohexyl sulfonamide synthesized in the same way as in Example 25, (i) from N-(3-methylaminopropyl)perfluorohexyl sulfonamide and 3,4-dichlorophenyl isocyanate, and 70 g of fully dehydrated methyl Cellosolve were weighed into a 100 ml three-necked round-bottomed flask equipped with a cooling condenser and a stirrer, and were heated to form a solution. At 80° C., 3 g (0.016 mole) of a 28% methanol solution of sodium methylate was added dropwise to the solution, and the mixture was heated to 110° C. to remove methanol. Thereafter, 1.75 g (0.08 mole) of 1,11-dichloro-3,6,9-trioxaundecane was gradually added. After the reaction was carried out at 90° C. for 8 hours, the methyl Cellosolve was distilled off under reduced pressure. The paste-like residue was dissolved in 100 ml of ethanol, and 10 g of Amberlite CG-400 Type-1 was added. The mixture was stirred at room temperature for 1 hour. The ion exchange resin was separated by filtration, and ethanol was distilled off under reduced pressure to give 11.1 g of a slightly yellow paste.

| Elemental analysis (%): | C | H | N |
|---|---|---|---|
| Found: | 34.2 | 2.8 | 5.5 |
| Calculated: | 34.2 | 2.9 | 5.7 |

NMR spectrum ($CD_3OC$ solvent, TMS standard): 1.78 ppm (m, 4H), 2.94 ppm (s, 6H), 3.10-3.40 ppm (m, 12H), 3.60 ppm (m, 12H), 7.20-7.85 ppm (m, 6H).

EXAMPLE 27

Synthesis of the following compound:

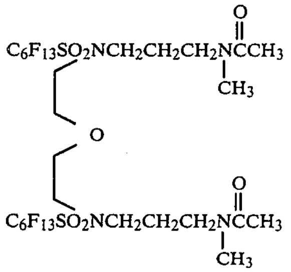

(i) Synthesis of the following compound:

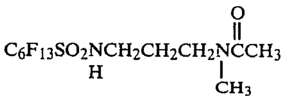

Into a 300 ml three-necked round-bottomed flask equipped with a silica gel dry tube and a stirrer were weighed 90 g (0.191 mole) of N-(3-methylamino-propyl)perfluorohexyl sulfonamide and 134 g of pyridine, and with vigorous stirring at room temperature, 29.3 g (0.287 mole) of acetic anhydride was added dropwise gradually. After the addition, the mixture was stirred at room temperature for 3 hours, and pyridine was distilled off under reduced pressure. Distilled water (150 ml) was added to the resulting viscous solid residue to age the crystals. The white crystals were collected by filtration, washed with water, and dried under reduced pressure at 70° C. The amount of the white crystals obtained was 100 g.

Melting point: 77.0°-78.5° C.

| Elemental analysis (%): | C | H | N |
|---|---|---|---|
| Found: | 28.0 | 2.4 | 5.7 |
| Calculated: | 28.1 | 2.5 | 5.5 |

IR spectrum: 1370 $cm^{-1}$ ($—SO_3N<$, $\nu$ as), 1640 $cm^{-1}$ ($—CON<$).

NMR spectrum ($CD_3COCD_3$ solvent; TMS standard): 1.83 ppm (m, 2H), 2.04 ppm (s, 3H), 3.05 ppm (s, 3H), 3.27 ppm (t, 2H), 3.48 ppm (t, 2H).

(ii) Synthesis of the following compound:

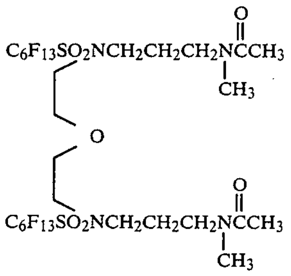

In an atmosphere of nitrogen, 10.2 g (0.02 mole) of N-[3-(N-methylacetamino)propyl]perfluorohexyl sulfonamide and 80 g of fully dehydrated methyl Cellosolve were weighed into a 100 ml three-necked round-bottomed flask equipped with a cooling condenser and a stirrer, and they were heated to form a solution. At 90° C., 4.6 g (0.024 mole) of a 28% methanol solution of sodium methylate was added dropwise to the solution, and the mixture was heated to 110° C. to distill off the methanol. Then, 1.7 g (0.012 mole) of bis(2-chloroethyl) ether was gradually added, and the reaction was carried out at 90° C. for 8 hours. The reaction mixture was cooled to room temperature, and the precipitated sodium chloride was separated by filtration. The methyl Cellosolve was distilled off, and the residue was dissolved in 100 ml of ethanol. Ten grams of Amberlite CG-400 Type-1 was added, and the mixture was stirred at room temperature for 1 hour. The ion exchange resin was separated by filtration, and the ethanol was distilled off under reduced pressure to give 10.1 g of a slightly yellow solid.

Melting point: 53.5° C.

| Elemental analysis (%): | C | H | N |
|---|---|---|---|
| Found: | 30.6 | 2.7 | 5.0 |
| Calculated: | 30.7 | 2.9 | 5.1 |

NMR spectrum ($CD_3OD$ solvent, TMS standard): 1.80 ppm (m, 4H), 2.08 ppm (d, 6H), 2.96 ppm (d, 6H), 3.20-3.50 ppm (m, 12H), 3.61 ppm (t, 4H).

EXAMPLE 28

Synthesis of the following compound:

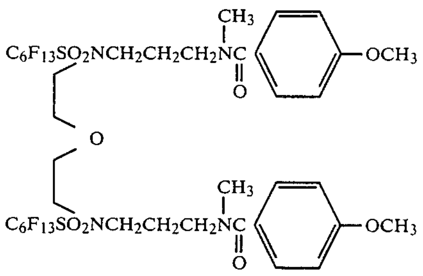

(i) Synthesis of the following compound:

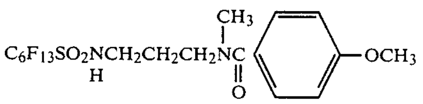

Into a three-necked round-bottomed flask equipped with a dry silica gel tube and a stirrer were weighed 62.8 g (0.134 mole) of N-(3-methylaminopropyl)perfluorohexyl sulfonamide, 14.9 g (0.147 mole) of triethylamine and 300 ml of dehydrated tetrahydrofuran. With stirring at 15° C., 25 g (0.147 mole) of p-methoxybenzoyl chloride was added gradually. The reaction was carried out at 30° C. for 4 hours. Tetrahydrofuran was removed under reduced pressure. The white solid residue was recrystallized from ethanol/water (7/2 V/V) to purity it.

Amount yielded: 74.9 g

Melting point: 121°-122° C.

| Elemental analysis (%): | C | H | N |
|---|---|---|---|
| Found: | 35.9 | 2.8 | 4.6 |
| Calculated: | 35.8 | 2.8 | 4.6 |

NMR spectrum ($CD_3COCD_3$ solvent, TMS standard): 1.99 ppm (m, 2H), 3.02 ppm (s, 3H), 3.33 ppm (t, 2H), 3.58 ppm (t, 2H), 3.81 ppm (s, 3H), 7.21 ppm (m, 4H).

(ii) Synthesis of the following compound:

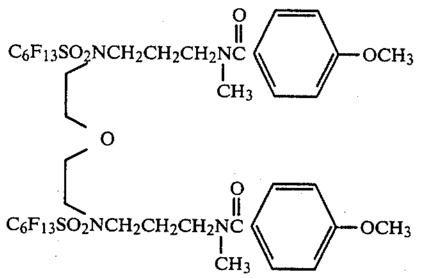

The above compound was prepared in the same way as in Example 27, (ii) using N-[N-methyl-N'-(p-methoxybenzoyl)-3-aminopropyl]perfluorohexyl sulfonamide obtained in Example 28, (i) and bis[2-chloroethyl)ether.

Melting point: 59°-61° C.

| Elemental analysis (%): | C | H | N |
|---|---|---|---|
| Found | 37.4 | 3.7 | 4.5 |
| Calculated: | 37.4 | 3.4 | 4.4 |

NMR spectrum ($CD_3COCD_3$ solvent, TMS standard): 1.99 ppm (m, 4H), 3.02 ppm (s, 6H), 3.39 ppm (t, 4H), 3.50 ppm (m, 8H), 3.60 ppm (t, 4H), 3.81 (s, 6H), 7.20 ppm (m, 8H).

EXAMPLES 29 TO 44

Table 4 summarizes the structural formulae and melting points of the compounds of this invention synthesized in the same way as in Examples 25 to 28.

TABLE 4

| Example No. | Structural formula | Melting point (°C.) |
|---|---|---|
| 29 | 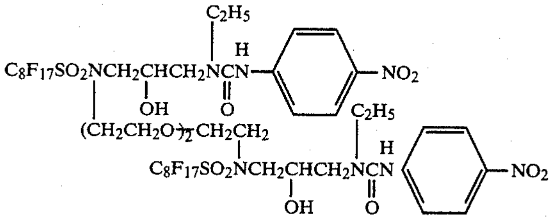 | Paste(1) |
| 30 | 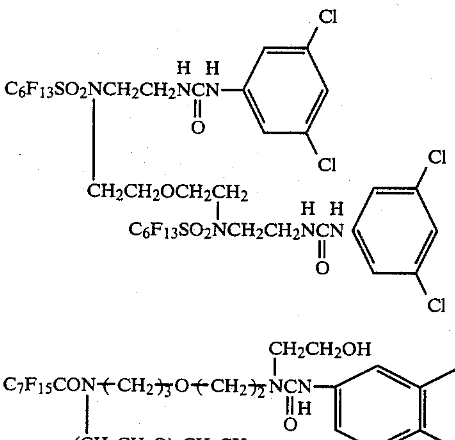 | 38-39 |
| 31 | 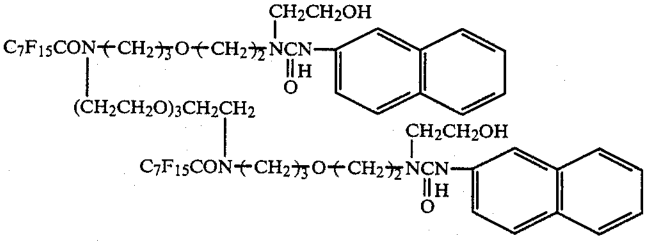 | Paste(2) |

TABLE 4-continued
| Example No. | Structural formula | Melting point (°C.) |
|---|---|---|
| 32 | 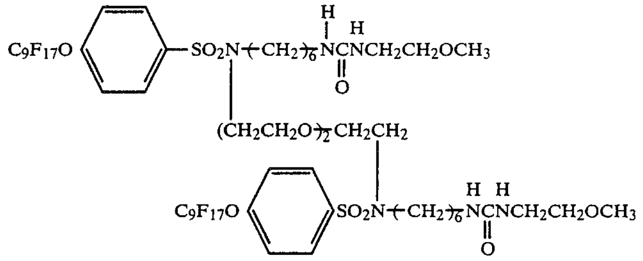 | Paste(3) |
| 33 | 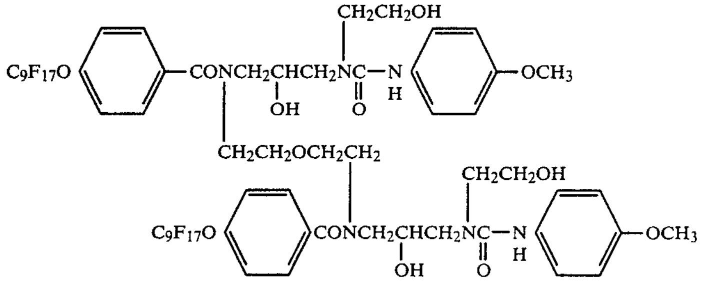 | 59-60 |
| 34 | 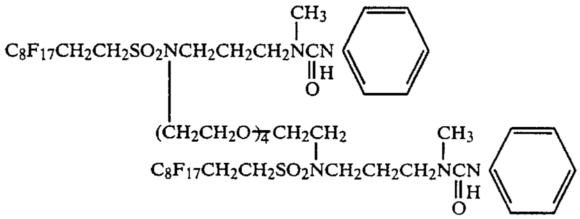 | Paste(4) |
| 35 | 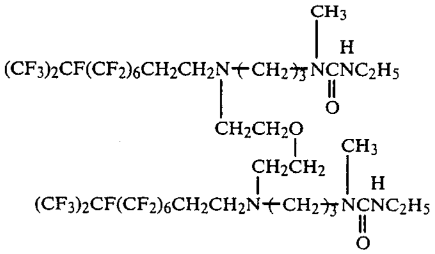 | 73-74 |
| 36 | 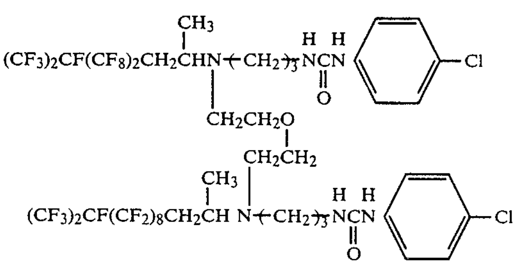 | 44-45 |
| 37 | 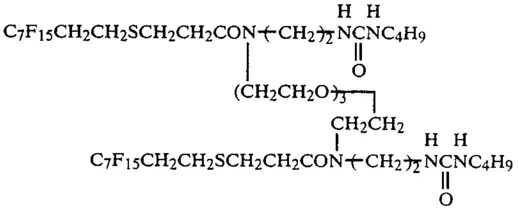 | Paste(5) |

TABLE 4-continued
| Example No. | Structural formula | Melting point (°C.) |
|---|---|---|
| 38 | 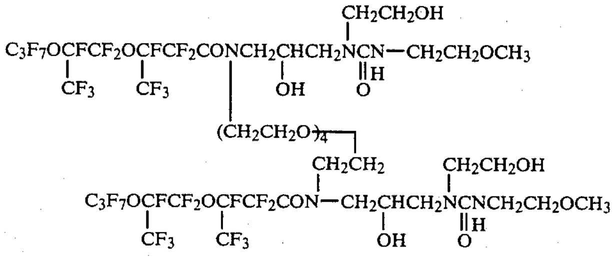 | Paste(6) |
| 39 | 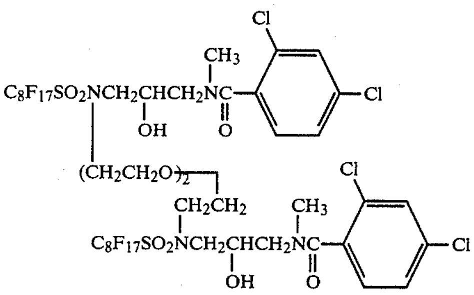 | 42–43 |
| 40 | 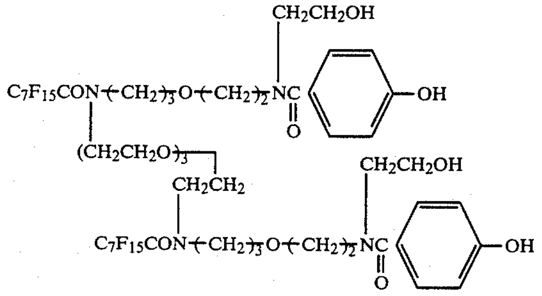 | Paste(7) |
| 41 | 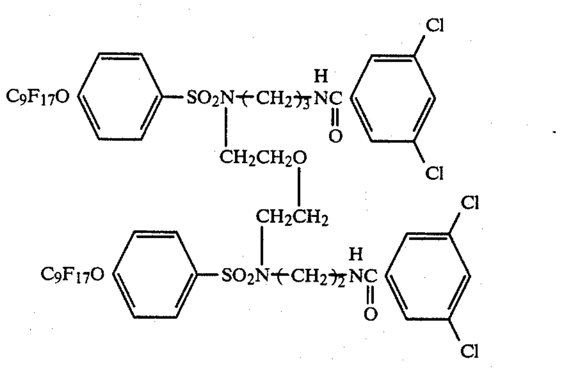 | 67–68 |
| 42 | 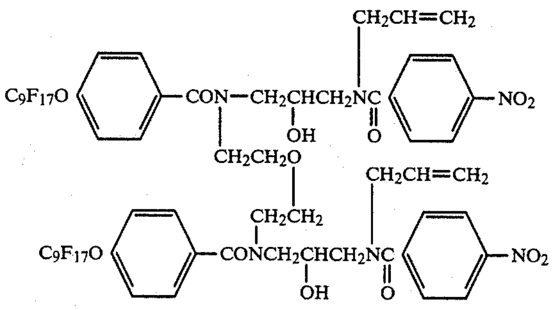 | 71–73 |

TABLE 4-continued

| Example No. | Structural formula | Melting point (°C.) |
|---|---|---|
| 43 | 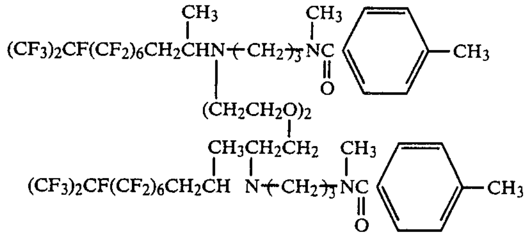 | 49-51 |
| 44 | 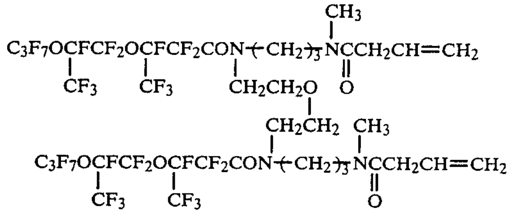 | 53-55 |

Note

| | | |
|---|---|---|
| (1)Elemental | Found: | C, 33.7; H, 2.6; N, 6.8 |
| analysis (%): | Calcd.: | C, 33.6; H, 2.7; N, 6.8 |
| (2)Elemental | Found: | C, 44.7; H, 3.8; N, 5.3 |
| analysis (%): | Calcd.: | C, 44.7; H, 3.8; N, 5.2 |
| (3)Elemental | Found: | C, 37.5; H, 3.5; N, 4.5 |
| analysis (%): | Calcd.: | C, 37.4; H, 3.5; N, 4.7 |
| (4)Elemental | Found | C, 38.3; H, 3.6; N, 5.2 |
| analysis (%): | Calcd.: | C, 38.1; H, 3.5; N, 5.1 |
| (5)Elemental | Found: | C, 38.3; H, 3.3; N, 5.7 |
| analysis (%): | Calcd.: | C, 38.5; H, 3.6; N, 5.9 |
| (6)Elemental | Found: | C, 33.5; H, 3.3; N, 5.0 |
| analysis (%): | Calcd.: | C, 33.3; H, 3.4; N, 4.9 |
| (7)Elemental | Found: | C, 41.0; H, 3.4; N, 3.6 |
| analysis (%): | Calcd.: | C, 41.2; H, 3.7; N, 3.7 |

EXAMPLE 45

Synthesis of the following compound:

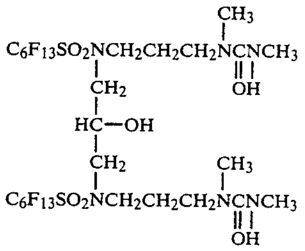

Into a 100 ml three-necked round-bottomed flask equipped with a cooling condenser and a stirrer were weighed 10 g (0.019 mole) of N-[3-(1,3-dimethylureido)propyl]perfluorohexyl sulfonamide and 70 g of fully dehydrated methyl Cellosolve, and they were heated to form a solution. At 80° C., 3.7 g (0.019 mole) of a 28% methanol solution of sodium methylate was added dropwise to the solution. The mixture was heated to 110° C. to remove methanol, and 1.2 g (0.0095 mole) of 1,3-dichloro-2-hydroxypropane was added gradually. The reaction was carried out at 90° C. for 8 hours, and then the methyl Cellosolve was distilled of under reduced pressure. The paste-like residue was dissolved in 100 ml of acetone, and the precipitated sodium chloride was separated by filtration. By distilling off acetone under reduced pressure, 10.3 g of a slightly yellow paste was obtained.

| Elemental analysis (%): | C | H | N |
|---|---|---|---|
| Found: | 29.0 | 2.9 | 7.8 |
| Calculated: | 29.2 | 2.9 | 7.6 |

NMR spectrum ($CD_3OD$ solvent, TMS standard): 1.80 ppm (m, 4H), 2.75 ppm (s, 6H), 2.90 ppm (s, 6H), 3.40 ppm (m, 12H), 3.91 ppm (m, 1H).

EXAMPLE 46

Synthesis of the following compound:

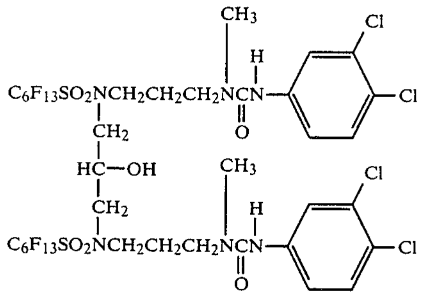

Ten grams (0.0155 mole) of N-{3-[1-methyl-3-(3,4-dichlorophenyl)ureido]propyl}perfluorohexyl sulfonamide synthesized in the same way as in Example 1, (ii) using N-(3-methylaminopropyl)perfluorohexyl sulfonamide and 3,4-dichlorophenyl isocyanate, and 70 g of fully dehydrated methyl Cellosolve were weighed into a 100 ml three-necked round-bottomed flask equipped with a cooling condenser and a stirrer, and heated to form a solution. At 80° C., 3 g (0.016 mole) of a 28% methanol solution of sodium methylate was added dropwise. The mixture was heated to 110° C. to remove methanol. Then, 1.0 g (0.08 mole) of 1,3-dichloro-2-hydroxypropane was gradually added. After carrying out the reaction at 90° C. for 8 hours, the methyl Cellosolve was distilled off under reduced pressure. The paste-like residue was dissolved in 100 ml of acetone. The precipitated sodium chloride was separated by filtration, and acetone was distilled off under reeuced pressure to give 11 g of a slightly yellow paste.

| Elemental analysis (%): | C | H | N |
|---|---|---|---|
| Found: | 33.1 | 2.4 | 5.9 |
| Calculated: | 32.4 | 2.3 | 6.1 |

NMR spectrum ($CD_3OD$ solvent, TMS standard): 1.78 ppm (m, 4H), 2.94 ppm (s, 6H), 3.60 ppm (m, 12H), 3.96 ppm (m, 1H), 7.20–7.85 ppm (m, 6H).

EXAMPLE 47

Synthesis of the following compound:

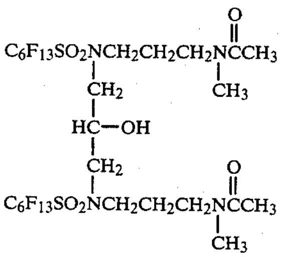

Into a 100 ml three-necked round-bottomed flask equipped with a cooling condenser and a stirrer were weighed 10.2 g (0.02 mole) of N-[3-(N-methylacetamino)propyl]perfluorohexyl sulfonamide and 80 g of fully dehydrated methyl Cellosolve in an atmosphere of nitrogen, and they were heated to form a solution. At 90° C., 4.6 g (0.024 mole) of a 28% methanol solution of sodium methylate was added dropwise to the solution. The mixture was heated to 110° C. to distill off methanol. Then, 1.5 g (0.012 mole) of 1,3-dichloro-2-hydroxypropane was added gradually. At 90° C., the mixture was reacted for 8 hours. The reaction mixture was then cooled to room temperature, and the precipitated sodium chloride was separated by filtration. The methyl Cellosolve was distilled off, and the residue was dissolved in acetone. The precipitated sodium chloride was again separated by filtration. By distilling off acetone, 10.8 g of a yellow paste was obtained.

| Elemental analysis (%): | C | H | N |
|---|---|---|---|
| Found: | 31.0 | 2.7 | 5.0 |
| Calculated: | 30.0 | 2.8 | 5.2 |

NMR spectrum ($CD_3OD$ solvent, TMS standard): 2.00 ppm (m, 4H), 2.09 ppm (s, 6H), 3.05 ppm (s, 6H), 3.30–3.75 ppm (m, 12H), 4.00 ppm (m, 1H).

EXAMPLES 48 TO 58

Table 5 summarizes the structural formulae and melting points of the compounds of this invention synthesized in the same way as in Examples 45 to 47.

TABLE 5

| Example | Structural formula | Melting point (°C.) |
|---|---|---|
| 48 | 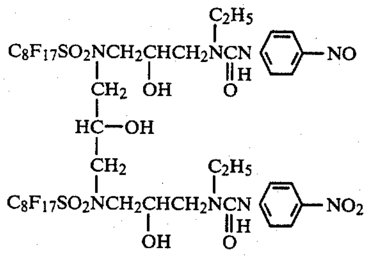 | 83–86 |
| 49 | 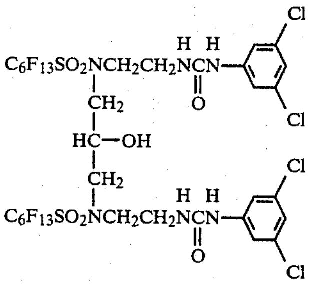 | 82–83 |

TABLE 5-continued
| Example | Structural formula | Melting point (°C.) |
|---|---|---|
| 50 | 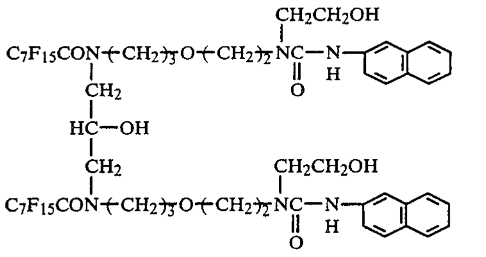 | 52-53 |
| 51 | 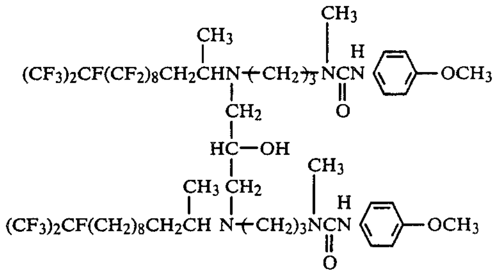 | 75-77 |
| 52 | 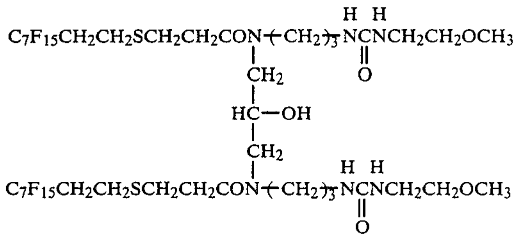 | 89-91 |
| 53 | 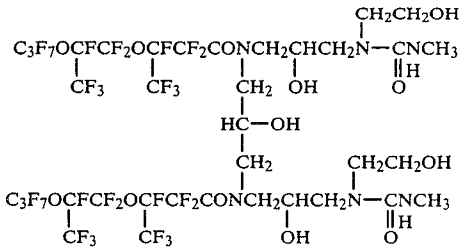 | 67-69 |
| 54 | 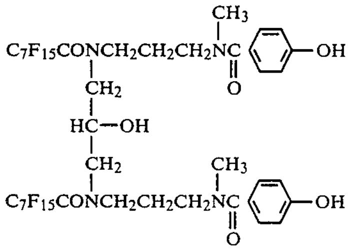 | 101-103 |
| 55 | 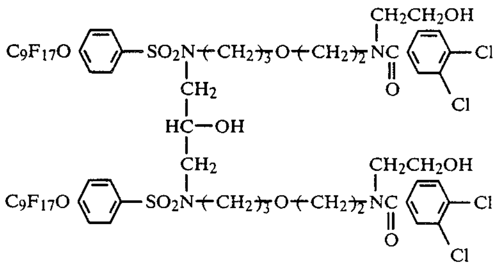 | 64-66 |

TABLE 5-continued

| Example | Structural formula | Melting point (°C.) |
|---|---|---|
| 56 | 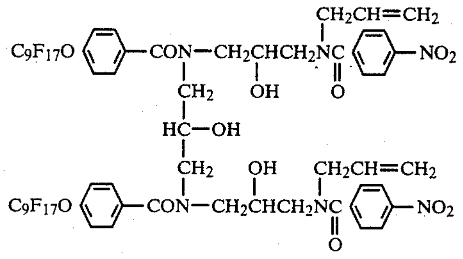 | 95–97 |
| 57 | 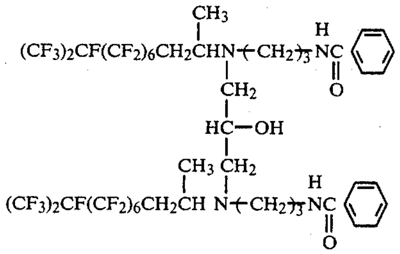 | 49–51 |
| 58 | 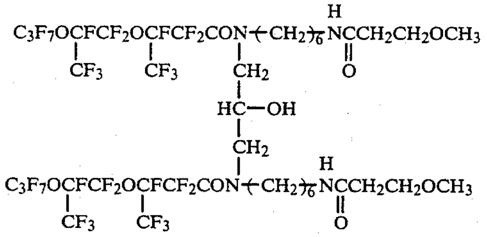 | 43–44 |

EXAMPLE 59

Synthesis of the following compound:

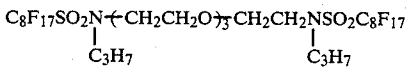

(i) Synthesis of

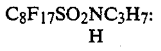

Into a 2-liter three-necked round-bottomed flask equipped with a stirrer and a drying tube were weighed 150 g (2.54 moles) of n-propylamine and 400 g of isopropyl ether. The temperature was adjusted to less than 50° C., and 510 g (1.02 moles) of perfluorooctanesulfonyl fluoride was added dropwise from a dropping funnel with vigorous stirring. After the addition, the mixture was further stirred for 3 hours at a temperature in the range of 50° to 60° C. The reaction solution was transferred to a separating funnel, and washed with 200 g of 6N HCl. The isopropyl ether layer was washed three times using 300 ml of distilled water each time. Then, 50 g of anhydrous sodium sulfate was added, and the washed product was dried at room temperature for one day. The isopropyl ether was distilled off, and the resulting reddish brown viscous solid was recrystallized from ethanol/chloroform (1/1 V/V) to give 503 g of colorless plate-like crystals.

| Elemental analysis (%): | C | H | N |
|---|---|---|---|
| Found: | 24.6 | 2.7 | 1.4 |
| Calculated: | 24.4 | 2.6 | 1.5 |

IR spectrum: 1370 $cm^{-1}$ ($-SO_2N<$, $\nu$ as).

(ii) Synthesis of the following compound:

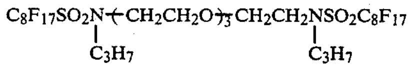

Ten grams (0.0185 mole) of N-propylperfluorooctanesulfonamide and 70 g of fully dehydrated methyl Cellosolve were weighed into a 100 ml three-necked round-bottomed flask equipped with a cooling condenser and a stirrer, and heated to form a solution. At 80° C., 3.9 g (0.02 mole) of a 28% methanol solution of sodium methylate was added dropwise to the solution. The mixture was heated to 110° C. to remove methanol. Then, 2.34 g (0.02 mole) of 1, 11-dichloro-3,6,9-trioxaundecane was gradually added, and the mixture was reacted at 90° C. for 8 hours. The methyl Cellosolve was distilled off under reduced pressure. To the paste-like residue was added 100 ml of ethanol/acetone (1/1 V/V), and the precipitated sodium chloride was separated by filtration. Five grams of Amberlite CG-400 Type -1 was added to the filtrate, and the mixture was stirred for one hour at room temperature. The ion exchange resin was separated by filtration, and ethanol was distilled off under reduced pressure. The white solid residue was recrystallized from chloroform/n-hexane.

Amount yielded: 10.2 g

Decomposition temperature: 210° C.

| Elemental analysis (%): | C | H | N |
|---|---|---|---|
| Found: | 28.8 | 2.6 | 2.2 |
| Calculated: | 29.0 | 2.4 | 2.3 |

NMR spectrum ($CD_3OD$ solvent, TMS standard): 1.90 ppm (t, 6H), 2.71 ppm (m, 4H), 3.04 ppm (t, 4H), 3.63 ppm (m, 16H).

EXAMPLE 60

Synthesis of the following compound:

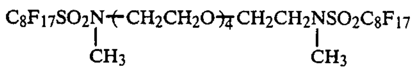

(i) Synthesis of the following compound:

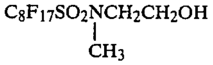

Into a 500 ml three-necked round-bottomed flask equipped with a cooling condenser and a stirrer were weighed 52.3 g (0.1 mole) of N-methylperfluorooctanesulfonamide and 250 g of methyl Cellosolve, and they were heated to form a solution. At 80° C., 21.2 g (0.11 mole) of a 28% methanol solution of sodium methylate was added dropwise. The mixture was heated to 110° C. to remove methanol. Then, 8.8 g (0.11 mole) of ethylene chlorohydrin was gradually added, and the reaction was carried out at 90° C. for 8 hours. The methyl Cellosolve was distilled off under reduced pressure. Ethanol was added to the residue, and the precipitated sodium chloride was separated by filtration. Ethanol was distilled off, and the residue was recrystallized from chloroform to give 53 g of a white solid.

-continued

| Elemental analysis (%): | C | H | N |
|---|---|---|---|
| Found: | 23.7 | 1.4 | 2.4 |
| Calculated: | 23.7 | 1.4 | 2.5 |

NMR spectrum ($CD_3OD$ solvent, TMS standard): 3.04 ppm (s, 3H), 3.12 ppm (t, 2H), 3.40 ppm (t, 2H).

(ii) Synthesis of the following compound:

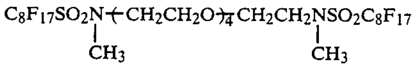

In an atmosphere of nitrogen, 5.57 g (0.01 mole) of N-methyl-N-hydroxyethylperfluorooctanesulfonamide, 0.58 g (0.012 mole) of 50% sodium hydride, and 40 ml of tetrahydrofuran were weighed into a 100 ml three-necked round-bottomed flask equipped with a cooling condenser and a stirrer, and with vigorous stirring, 20 ml of a tetrahydrofuran solution of 3.63 g (0.006 mole) of tetraethylene glycol ditosylate was added dropwise. The mixture was refluxed for 5 hours in an atmosphere of nitrogen, and then cooled. The precipitated sodium tosylate was separated by filtration. The tetrahydrofuran was distilled off under reduced pressure, and 50 ml of ethanol was added to the resulting white solid residue. The solution was treated with 5 g of Amberlite CG-400 Type-1. The ion exchange resin was separated by filtration, and ethanol was distilled off under reduced pressure. The resulting white solid residue was recrystallized from chloroform/n-hexane.

Amount yielded: 5.4 g

| Elemental analysis (%): | C | H | N |
|---|---|---|---|
| Found: | 27.3 | 2.3 | 2.2 |
| Calculated: | 27.4 | 2.1 | 2.3 |

NMR spectrum ($CD_3OD$ solvent, TMS standard): 3.07 ppm (s, 6H), 3.64 ppm (m, 20H).

EXAMPLES 61 TO 71

Table 6 summarizes the structural formulae and melting points of the compounds of this invention synthesized in the same way as in Examples 59 (method A) and 60 (method B).

TABLE 6

| Example | Structural formula | Melting point (°C.) |
|---|---|---|
| 61 | 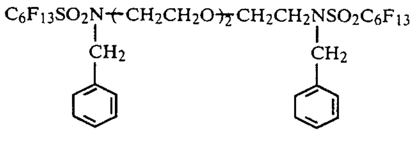 | 34-36[1] |
| 62 | 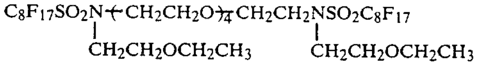 | Paste[2] |
| 63 | 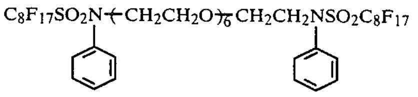 | Paste[3] |
| 64 | 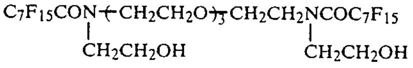 | Paste[4] |

TABLE 6-continued

| Example | Structural formula | Melting point (°C.) |
|---|---|---|
| 65 | 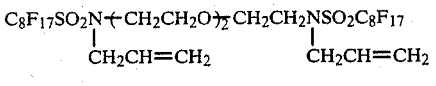 | Paste[5] |
| 66 | 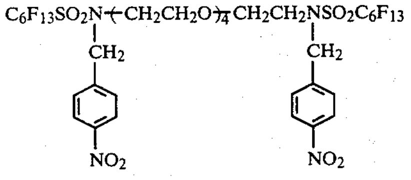 | Paste[6] |
| 67 | 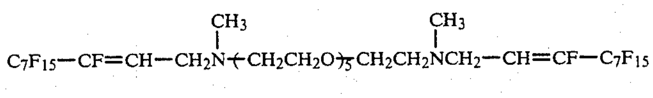 | Paste[7] |
| 68 | 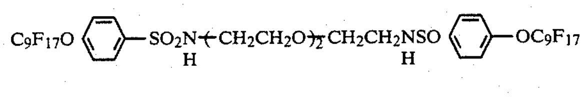 | Paste[8] |
| 69 | 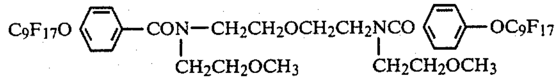 | 38–40 |
| 70 | 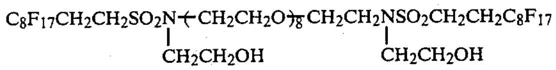 | Paste[9] |
| 71 | 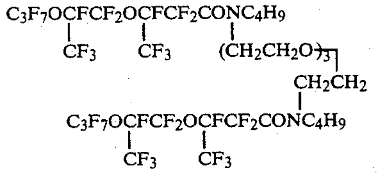 | Paste[10] |

Note

| | | | | |
|---|---|---|---|---|
| [1] Elemental analysis (%): | Found: | C, 35.2; | H, 2.3; | N, 2.5 |
| | Calcd.: | C, 35.2; | H, 2.4; | N, 2.6 |
| [2] Elemental analysis (%): | Found: | C, 30.4; | H, 2.7; | N, 2.2 |
| | Calcd.: | C, 30.3; | H, 2.8; | N, 2.1 |
| [3] Elemental analysis (%): | Found: | C, 34.8; | H, 2.6; | N, 2.1 |
| | Calcd.: | C, 35.0; | H, 2.6; | N, 1.9 |
| [4] Elemental analysis (%): | Found: | C, 31.2; | H, 2.5; | N, 2.6 |
| | Calcd.: | C, 31.3; | H, 2.5; | N, 2.6 |
| [5] Elemental analysis (%): | Found: | C, 28.4; | H, 1.9; | N, 2.3 |
| | Calcd.: | C, 28.2; | H, 1.8; | N, 2.3 |
| [6] Elemental analysis (%): | Found: | C, 35.2; | H, 2.3; | N, 4.6 |
| | Calcd.: | C, 35.4; | H, 2.3; | N, 4.6 |
| [7] Elemental analysis (%): | Found: | C, 35.0; | H, 3.3; | N, 2.5 |
| | Calcd.: | C, 35.2; | H, 3.2; | N, 2.5 |
| [8] Elemental analysis (%): | Found: | C, 32.5; | H, 1.8; | N, 2.2 |
| | Calcd.: | C, 32.7; | H, 1.7; | N, 2.1 |
| [9] Elemental analysis (%): | Found: | C, 34.4; | H, 3.8; | N, 2.0 |
| | Calcd.: | C, 34.4; | H, 3.7; | N, 1.9 |
| [10] Elemental analysis (%): | Found: | C, 31.8; | H, 2.6; | N, 2.0 |
| | Calcd.: | C, 31.8; | H, 2.5; | N, 2.1 |

EXAMPLES 72 TO 121

Chloroform solutions ($7.0\times10^{-4}$M, 20 ml) of the fluoroalkyl-containing compounds shown in Table 7 and aqueous solutions ($7.0\times10^{-4}$M, 20 ml) of metal salts (uranyl acetate, NaCl, $MgCl_2$, $CaCl_2$, $BaCl_2$, $CoCl_2$, $NiCl_2$, $CuCl_2$, $ZnCl_2$, $HgCl_2$) were prepared separately. Liquid-liquid extraction of the metal salts was carried out at 37° C. for 24 hours by stirring with a magnetic stirrer.

The amount extracted of each metal salt was determined by quantitatively analyzing the metal ion remaining in the aqueous solution (by the Arsenazo III method for a uranyl ion, and by an atomic absorptiometric method for other metal ions).

The results are also tabulated in Table 7.

TABLE 7

| Example No. | Fluoroalkyl-containing compound (*) | Amount extracted (%) UO2 | Na | Mg | Ca | Ba | Co | Ni | Cu | Zn | Hg |
|---|---|---|---|---|---|---|---|---|---|---|---|
| 72 | A | 16.0 | 0 | 0 | 0 | 30.3 | 0 | 0 | 0 | 0 | 0 |

TABLE 7-continued

| Example No. | Fluoroalkyl-containing compound (*) | Amount extracted (%) UO2 | Na | Mg | Ca | Ba | Co | Ni | Cu | Zn | Hg |
|---|---|---|---|---|---|---|---|---|---|---|---|
| 73 | B | 35.6 | 33.3 | 0 | 0 | 10.0 | 44.1 | 0 | 49.5 | 0 | 0 |
| 74 | C | 98.6 | 43.0 | 0 | 12.3 | 11.0 | 5.6 | 0 | 0 | 0 | 0 |
| 75 | D | 32.6 | 0 | 0 | 0 | 7.8 | 0 | 0 | 4.0 | 0 | 0 |
| 76 | E | 11.3 | 21.3 | 0 | 2.5 | 21.3 | 0 | 0 | 0 | 0 | 0 |
| 77 | F | 26.3 | 21.0 | 10.6 | 0 | 10.6 | 1.8 | 0 | 8.8 | 0 | 0 |
| 78 | G | 43.3 | 31.4 | 0 | 0 | 8.6 | 0 | 0 | 0 | 0 | 0 |
| 79 | H | 34.6 | 13.1 | 21.7 | 46.8 | 7.7 | 13.3 | 0 | 39.0 | 0 | 0 |
| 80 | I | 100 | 0 | 0 | 1.6 | 0 | 0 | 0 | 0 | 0 | 1.7 |
| 81 | J | 39.8 | 6.0 | 0 | 0 | 1.6 | 1.6 | 0 | 0.4 | 0 | 0 |
| 82 | K | 0 | 0 | 0 | 0 | 59.2 | 23.1 | 0 | 24.4 | 0 | 24.0 |
| 83 | L | 27.0 | 18.8 | 0 | 0 | 5.2 | 45.0 | 0 | 47.3 | 0 | 0 |
| 84 | M | 20.1 | 9.9 | 27.7 | 54.5 | 13.0 | 11.1 | 0 | 39.5 | 0 | 0 |
| 85 | 1 | 98.5 | 0 | 0 | 3.8 | 5.0 | 0 | 0 | 0 | 0 | 0 |
| 86 | 5 | 58.2 | 9.1 | 1.0 | 5.1 | 0 | 0 | 0 | 0 | 0 | 5.5 |
| 87 | 7 | 69.2 | 3.4 | 0 | 0 | 0 | 11.7 | 0 | 30.0 | 0 | 6.5 |
| 88 | 9 | 74.4 | 3.1 | 0 | 0 | 0 | 40.9 | 0 | 28.8 | 0 | 0 |
| 89 | 10 | 36.0 | 0 | 0 | 0 | 13.6 | 0 | 0 | 0 | 0 | 0 |
| 90 | 14 | 44.8 | 0 | 0 | 1.7 | 0 | 0 | 0 | 0 | 0 | 0 |
| 91 | 16 | 100 | 0 | 5.3 | 4.4 | 0 | 0 | 0 | 0 | 0 | 1.7 |
| 92 | 17 | 56.0 | 3.0 | 0 | 2.2 | 11.2 | 10.0 | 0 | 0 | 0 | 0 |
| 93 | 19 | 66.3 | 0 | 0 | 0 | 1.2 | 17.7 | 0 | 19.3 | 0 | 0 |
| 94 | 21 | 81.0 | 0 | 0 | 0 | 0 | 20.0 | 0 | 15.3 | 0 | 0 |
| 95 | 23 | 94.4 | 0 | 0 | 4.3 | 5.4 | 0 | 0 | 14.7 | 0 | 0 |
| 96 | 24 | 50.9 | 0 | 0 | 10.1 | 10.1 | 33.1 | 0 | 38.3 | 0 | 0 |
| 97 | 25 | 93.7 | 0 | 0 | 5.1 | 0 | 1.8 | 0 | 0.4 | 0 | 0 |
| 98 | 26 | 79.8 | 1.0 | 0 | 4.0 | 0 | 2.7 | 0 | 0 | 0 | 1.3 |
| 99 | 27 | 63.0 | 0 | 0 | 8.8 | 4.2 | 4.6 | 0 | 0.7 | 0 | 0 |
| 100 | 28 | 93.2 | 0 | 0 | 1.0 | 2.2 | 76.4 | 0 | 86.8 | 0 | 0 |
| 101 | 31 | 97.1 | 0 | 0 | 0 | 0 | 70.0 | 0 | 43.7 | 0 | 0 |
| 102 | 32 | 54.4 | 0 | 0 | 0 | 0 | 30.9 | 0 | 79.8 | 0 | 0 |
| 103 | 34 | 91.0 | 0 | 9.9 | 4.0 | 9.2 | 83.0 | 0 | 80.9 | 0 | 0 |
| 104 | 36 | 85.2 | 0 | 0 | 3.3 | 4.1 | 50.0 | 0 | 41.2 | 0 | 0 |
| 105 | 38 | 99.3 | 0 | 0 | 0 | 0 | 89.2 | 0 | 76.3 | 0 | 0 |
| 106 | 40 | 88.5 | 0 | 0 | 0 | 0 | 40.0 | 0 | 37.2 | 0 | 0 |
| 107 | 41 | 74.6 | 0 | 0 | 0 | 0 | 20.0 | 0 | 19.4 | 0 | 0 |
| 108 | 44 | 78.9 | 0 | 0 | 0 | 0 | 11.0 | 0 | 53.0 | 0 | 0 |
| 109 | 45 | 87.3 | 0 | 0 | 0 | 4.4 | 7.0 | 0 | 3.9 | 0 | 0 |
| 110 | 47 | 15.3 | 0 | 0 | 0 | 0 | 66.0 | 0 | 59.3 | 0 | 0 |
| 111 | 50 | 37.0 | 0 | 0 | 0 | 19.1 | 40.2 | 0 | 44.6 | 0 | 0 |
| 112 | 52 | 23.0 | 0 | 0 | 1.2 | 0 | 19.4 | 0 | 39.9 | 0 | 0 |
| 113 | 53 | 24.7 | 0 | 0 | 0 | 0 | 56.7 | 0 | 68.4 | 0 | 0 |
| 114 | 55 | 14.2 | 0 | 0 | 0 | 0 | 74.1 | 0 | 50.5 | 0 | 0 |
| 115 | 58 | 21.3 | 0 | 0 | 0 | 0 | 50.0 | 0 | 37.2 | 0 | 0 |
| 116 | 59 | 94.5 | 23.3 | 0 | 0 | 4.3 | 78.6 | 0 | 67.3 | 0 | 0 |
| 117 | 61 | 84.7 | 20.9 | 0 | 0 | 3.3 | 64.7 | 0 | 52.0 | 0 | 0 |
| 118 | 64 | 91.1 | 0 | 0 | 0 | 0 | 37.2 | 0 | 40.6 | 0 | 0 |
| 119 | 66 | 94.2 | 0 | 0 | 0 | 0 | 78.1 | 0 | 39.2 | 0 | 0 |
| 120 | 68 | 65.2 | 0 | 0 | 0 | 0 | 37.9 | 0 | 41.0 | 0 | 0 |
| 121 | 71 | 99.7 | 0 | 0 | 0 | 0 | 70.7 | 0 | 81.2 | 0 | 0 |

Note
The alphabets A, B, . . . M in the column of the fluoro-alkyl-containing compound in Table 7 show the compounds given in Table 1, and the numbers 1, 5, . . . 71 represent those compounds which were synthesized in the correspondingly numbered Examples.

For comparison, the extracting experiment was carried out using the following compound.

$$C_8H_{17}SO_2\underset{\displaystyle C_3H_7}{\underset{|}{N}}\!-\!(CH_2CH_2O)_3\!-\!CH_2CH_2\underset{\displaystyle C_3H_7}{\underset{|}{N}}SO_2C_8F_{17}$$

The amounts of these metals ions extracted by this comparative experiment was 0% (cf. Examples 59 and 116). The results show that the presence of a fluoroalkyl group is essential in order to obtain an extracting ability, and suggest that the extraction is effected in accordance with the mechanism already explained.

EXAMPLES 122 TO 135

A solution of uranyl acetate in artificial sea water ($7.0\times10^{-4}$M, 20 ml; adjusted to pH 8.0 by sodium carbonate) was prepared, and liquid-liquid extraction of the above solution with a chloroform solution ($7.0\times10^{-4}$M, 20 ml) of each of the fluoroalkyl-containing compounds shown in Table 8 was carried out under the same conditions as in Examples 72 to 121. After the extraction, the chloroform layer was contacted with 10 ml of a 20% aqueous solution of ammonium carbonate for 20 minutes with stirring to effect back-extraction. The amount of an uranyl ion extracted from the artificial sea water the amount of back-extraction are shown in Table 8.

The artificial sea water used contained 25 g of NaCl, 4 g of $Na_2SO_4$, 1.6 g of $CaCL_2.2H_2O$, and 11 g of $MgCl_2.6H_2O$ per liter.

TABLE 8

| Example | Fluoroalkyl-containing compound (*) | Amount extracted (%) UO2 | Na | Mg | Ca | Amount back-extracted UO2 (%) |
|---|---|---|---|---|---|---|
| 122 | C | 62.0 | 20 | 0 | 0 | 61.0 |
| 123 | I | 90.1 | 0 | 0 | 0 | 88.0 |
| 124 | 1 | 97.0 | 0 | 0 | 2.0 | 90.3 |

TABLE 8-continued

| Example | Fluoroalkyl-containing compound (*) | Amount extracted (%) | | | | Amount back-extracted |
|---|---|---|---|---|---|---|
| | | $UO_2$ | Na | Mg | Ca | $UO_2$ (%) |
| 125 | 9 | 63.7 | 1.0 | 0 | 0 | 57.5 |
| 126 | 16 | 95.2 | 0 | 2.0 | 0 | 95.0 |
| 127 | 23 | 90.0 | 0 | 0 | 0.5 | 88.8 |
| 128 | 25 | 87.0 | 0 | 0 | 0.8 | 85.2 |
| 129 | 28 | 78.9 | 0 | 0.9 | 0 | 78.5 |
| 130 | 31 | 91.5 | 0 | 0 | 0 | 87.6 |
| 131 | 34 | 85.4 | 0 | 9.3 | 0 | 83.6 |
| 132 | 36 | 79.1 | 0 | 0 | 1.0 | 79.0 |
| 133 | 38 | 100 | 0 | 0 | 0 | 94.7 |
| 134 | 59 | 57.7 | 10.6 | 0 | 0 | 54.9 |
| 135 | 66 | 89.4 | 0 | 0 | 0 | 89.4 |

(*)The alphabets and numerals are the same as the footnote to Table 7.

The results show that the uranyl ion can be trapped and recovered by the method of this invention without being affected by the existing metal ion. Furthermore, the chloroform solutions of the fluoro-alkyl-containing compounds shown in Table 8 could be repeatedly used ten times without an appreciable decrease in ability.

EXAMPLES 136 AND 137

A solution of uranyl acetate in artificial sea water ($7.0\times10^{-4}$M, 20 ml; the composition of the artificial sea water was the same as in Examples 122 to 135), and 5 mg of each of the fluoroalkyl-containing compounds shown in Table 9 was added to the solution. The mixture was stirred at 40° C. for 48 hours to perform liquid-solid extraction. The fluoroalkyl-containing compound was collected by filtration, and back-extracted by dipping it in 10 ml of a 20% aqueous solution of ammonium carbonate for 20 minutes. The amount of the uranyl ion extracted from the artificial sea water and that back-extracted are shown in Table 9.

TABLE 9

| Example | Fluoroalkyl-containing compound(*) | Amount of $UO_2$ extracted (%) | Amount of $UO_2$ back-extracted (%) |
|---|---|---|---|
| 136 | A | 54.0 | 49.7 |
| 137 | 36 | 46.7 | 43.8 |

(*)The alphabet and numeral are the same as the footnote to Table 7.

EXAMPLES 138 TO 143

A solution of uranyl acetate in artificial sea water ($7.0\times10^{-4}$M, 20 ml; the composition of artificial sea water was as described above) was prepared, and extracted in a liquid-liquid contacting mode with a dichloromethane solution ($7.0\times10^{-4}$M, 20 ml) of each of the fluoroalkyl-containing compounds shown in Table 10 under the same conditions as in Examples 72 to 121. The precipitate in the dichloroethane layer was collected by filtration, and dipped for 20 minutes in 10 ml of a 20% aqueous solution of ammonium carbonate to recovery the uranyl ion. The results are summarized in Table 10.

TABLE 10

| Example | Fluoroalkyl-containing compound(*) | Amount of $UO_2$ recovered (%) |
|---|---|---|
| 138 | C | 88.0 |
| 139 | I | 97.5 |
| 140 | 16 | 92.8 |
| 141 | 23 | 73.2 |
| 142 | 38 | 89.1 |

TABLE 10-continued

| Example | Fluoroalkyl-containing compound(*) | Amount of $UO_2$ recovered (%) |
|---|---|---|
| 143 | 66 | 95.2 |

(*)The alphabets and numerals are the same as the footnote to Table 7.

EXAMPLES 144 TO 150

The recovery of a uranyl ion by a liquid film method was carried out by the following procedure.

Two grams of sorbitan trioleate as a surfactant was dissolved in a chloroform solution ($1.0\times10^{-3}$M, 100 g) of each of the fluoroalkyl-containing compounds shown in Table 11, and then 200 g of a 10% aqueous solution of sodium carbonate was added. The mixture was stirred vigorously to form a w/o emulsion. The emulsion was added to a solution of uranyl acetate in artificial sea water ($1.0\times10^{-3}$M, 2 kg; the composition of artificial sea water was the same as above). They were contacted for 30 minutes with stirring at a speed of 150 rpm, and the mixture was then allowed to stand for 10 minutes. The amount of the metallic ion remaining in the treated artificial sea water as an upper layer was measured. It was seen as shown in Table 11 that the uranyl ion was selectively recovered in the aqueous sodium carbonate solution.

TABLE 11

| Example | Fluoroalkyl-containing compounds(*) | Amount remaining (%) | | | |
|---|---|---|---|---|---|
| | | $UO_2$ | Na | Mg | Ca |
| 144 | I | 0 | 88.0 | 100 | 97.7 |
| 145 | 23 | 0 | 100 | 100 | 79.9 |
| 146 | 31 | 0 | 100 | 100 | 100 |
| 147 | 38 | 0 | 100 | 100 | 100 |
| 148 | 45 | 0 | 100 | 98.6 | 98.6 |
| 149 | 64 | 0 | 100 | 100 | 100 |
| 150 | 71 | 0 | 100 | 100 | 100 |

(*)The alphabet and numerals are the same as the footnote to Table 7.

EXAMPLES 151 AND 152

Catalytic action in a nucleophilic substitution reaction:

Into a 50 ml two-necked round-bottomed flask equipped with a cooling condenser and a stirrer were weighed 2.5 g (0.02 mole) of benzyl chloride, 2.0 g (0.04 mole) of sodium cyanide, 0.4 g of each of the compounds of the following formula

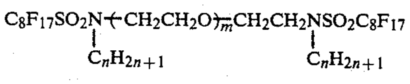

and 25 ml of acetonitrile. The reaction was carried out at 80° C. for 3 hours. After the reaction, the reaction mixture was allowed to cool. Diphenyl ether was added to the reaction mixture as an internal standard for gas chromatography. The resulting benzyl nitrile was quantitatively determined. The results are shown in Table 12.

TABLE 12

| Run | Additive | Amount (g) | Yield of benzyl nitrile (%) |
|---|---|---|---|
| Example 151 | n = 3, m = 3 | 0.4 | 82.2 |
| Example 152 | n = 2, m = 4 | 0.4 | 87.6 |
| Comparative Example 1 | None | — | 57.9 |
| Comparative | Dibenzo-18- | 0.5 | 98.7 |

TABLE 12-continued

| Run | Additive | Amount (g) | Yield of benzyl nitrile (%) |
|---|---|---|---|
| Example 2 | crown-6 | | |

The catalytic effect of the fluorine-containing compound of this invention can be clearly seen from Table 12.

EXAMPLES 153 TO 155

Catalytic activity in an eliminating reaction:

Into a 50 ml two-necked round-bottomed flask equipped with a cooling condenser and a stirrer were weighed 3.4 g (0.02 mole) of 1,2-dichloropropane, 2.0 g (0.04 mole) of sodium hydroxide, 25 ml of benzene, and 0.4 g of a compound of the following formula in accordance with this invention having the following formula.

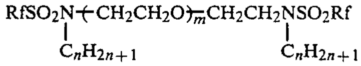

The mixture was stirred at 30° C. for 15 hours. Toluene as an internal standard for gas chromatography was added to the reaction mixture, and the total yield of 1-chloropropylene and 2-chloropropylene formed was determined. The results are shown in Table 13.

TABLE 13

| | Compound of this invention | | | | Yield of |
|---|---|---|---|---|---|
| Run | Rf | n | m | Amount added (g) | chloropropylenes (%) |
| Example 153 | $C_8F_{17}$— | 3 | 3 | 0.4 | 67.7 |
| Example 154 | $C_8F_{17}$— | 2 | 4 | 0.4 | 79.9 |
| Example 155 | $C_6F_{13}$— | 6 | 4 | 0.4 | 51.1 |
| Comparative Example 3 | | Not used | | | nearly zero |

The catalytic effect of the fluorine-containing compounds of this invention can be clearly seen from Table 13.

What is claimed is:

1. A method for recovering a cationic substance selected from the group consisting of metal ions, metal oxide ions, complex ions, amino acids and ammonium compounds, which comprises adding a water-insoluble organic solvent solution of a fluorine-containing compound containing both a fluoroalkyl group and a group having affinity for the cationic substance in its molecular structure and represented by the following general formula (I)

$$(\{Rf\text{-}(A)_a\text{-}Y\}(X)_b)_n(Z)_c \quad (I)$$

wherein

Rf is a fluoroalkyl group having 3 to 20 carbon atoms,

A is a polyvalent linking group having a valence of 2, 3 or 4, selected from the group consisting of an etheric oxygen atom, an etheric sulfur atom, a carbonyl group, a sulfonyl group, a tertiary nitrogen atom, a carbonamido group, a sulfonamide group, $-(CH_2)_p$ where p is an integer of 1 to 5,

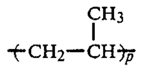

wherein p is an integer of 1 to 5,

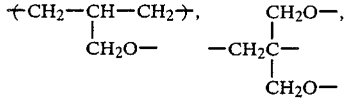

$-CH_2CH_2N<$, $-CH_2CH_2S-$, $-CH_2CH_2SO_2N<$, $-CH_2CH_2CON<$,

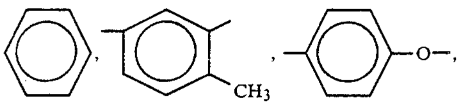

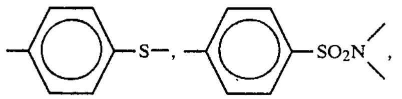

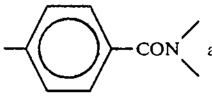

and

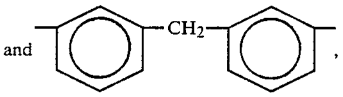

Y is a group having a valence of 1, 2 or 3 and alone or together with the group A has affinity for the cationic substance, and the functional group constituting Y is at least one member selected from the group consisting of a sulfonyl group, sulfonamido group, a carbonyl group, carbonamido group, a carbonyl ester group, amino group, hydroxyl group, a urethane linkage, a urea linkage and an ether linkage, X is an aliphatic or aromatic group having a valence of 1 which bonds to A or Y and which does not hinder the interaction of said compound with the cationic substance, Z is a polyvalent linking group having a valence of 2 or 3 which links two or three groups $(\{R_f\text{-}(A)_a\text{-}Y\}(X)_b)$ by bonding to A or Y in the two or three group $(\{R_f\text{-}(A)_a\text{-}Y\}(X)_b)$, a, b and c are 0 or 1 and are determined independently from each other, n is an integer of 1 to 3, and when n is 1, c is zero, to a liquid medium in which the cationic substance is dissolved or dispersed, and separating the cationic substance from the liquid medium by including it in an ionophore formed by the fluorine containing compound.

2. The method of claim 1 wherein Rf in formula I is a linear, branched linear, cyclic, or ring-containing linear perfluoroalkyl group, or a perfluoroalkyl group having an oxygen atom in the main chain.

3. The method of claim 1 wherein Z is

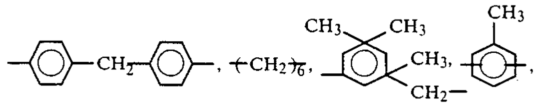

$-(CH_2CH_2O)_q CH_2CH_2-$ where q is an integer of 1 to 12,

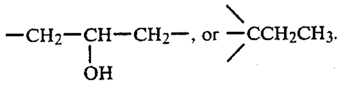

4. The method of claim 1 wherein the fluorine-containing compound including the cationic substance is separated as an upper or lower layer of the liquid medium.

5. The method of claim 1 wherein the fluorine-containing compound including the cationic substance or its solution is contacted with an aqueous solution of an inorganic acid or base to separate the ionic substance from the fluorine-containing compound.

6. The method of claim 1 wherein the fluorine-containing compound is a compound of the formula

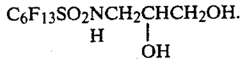

7. The method of claim 1 wherein the fluorine-containing compound is a compound of the following formula (II)

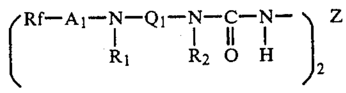
(II)

wherein $R_f$ is as defined above, $A_1$ is the polyvalent linking group A having a valence of 2, $R_1$ is a hydrogen atom, an alkyl group having 1 to 12 carbon atoms, a methoxyethyl group, an ethoxyethyl group, a group of the formula

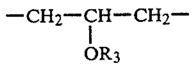

or a group of the formula $-(CH_2CH_2O)_r H$ where r is an integer of 1 to 5, $R_2$ is a hydrogen atom, or an alkyl or hydroxyalkyl group having 1 to 3 carbon atoms, $Q_1$ is $-(CH_2)_l$ where l is an integer of 2 to 6, $-(CH_2)_l O-(CH_2)_m$ where l and m are integers of 2 to 6, or

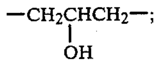

where $R_3$ represents a hydrogen atom or an alkyl group having 1 to 3 carbon atoms, and Z is a divalent linking group.

8. The method of claim 1 wherein the fluorine-containing compound is a compound of the following formula (III)

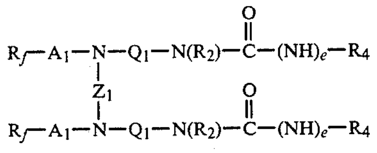
(III)

wherein $R_f$ is as defined above, $A_1$ is the polyvalent linking group A having a valence of 2, $Q_1$ is $-CH_2-_l$ wherein l is an integer of 2 to 6, $-CH_2-_l O-CH_2)_m$ where l and m are integers of 2 to 6, or

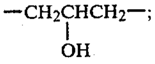

where $R_3$ is a hydrogen atom or an alkyl group having 1 to 3 carbon atoms, $R_2$ is a hydrogen atom, or an alkyl or hydroxyalkyl group having 1 to 3 carbon atoms, $R_4$ is an alkyl or alkenyl group having 1 to 6 carbon atoms, an alkyl group having 1 to 6 carbon atoms and 1 or 2 etheric oxygen atoms, or an aromatic group including a ring-substituted aromatic group, $Z_1$ is $-(CH_2CH_2O)_f CH_2CH_2-$ where f is an integer of 1 to 8, or

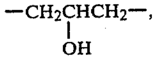

and e is 0 or 1.

9. The method of claim 1 wherein the fluorine containing compound has the following formula (IV)

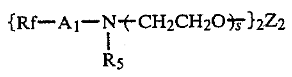
(IV)

wherein

Rf is as defined above, $A_1$ is the polyvalent linking group A having a valence of 2, $R_5$ is a hydrogen atom, an alkyl, hydroxyalkyl or alkenyl group having 1 to 16 carbon atoms, a $C_{1-16}$ alkyl group having 1 or 2 etheric oxygen atoms, an aromatic group, or a group containing an aromatic ring, $Z_2$ is $-CH_2CH_2OCH_2CH_2-$, and s is an integer of 1 to 6.

10. The method of any one of claims 7, 8 or 9 where $A_1$ is $-(B)_h SO_2-$ or $-(B)_h CO$ where B is $-CH_2CH_2-$, or

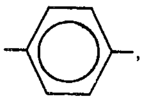

and h is 0 or 1.

11. The method of claim 1 wherein the fluorine-containing compound is a compound selected from the group consisting of the following compounds A–N:

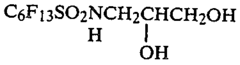
A

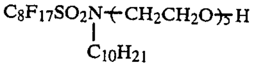
B

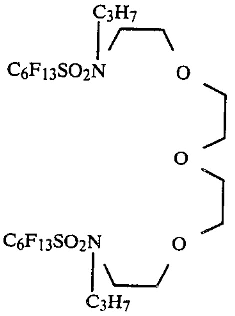
C

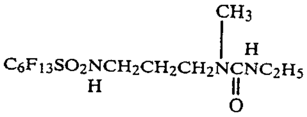
D

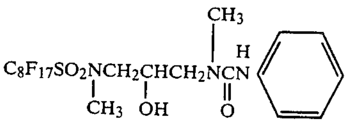
E

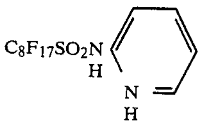
F

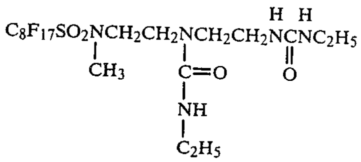
G

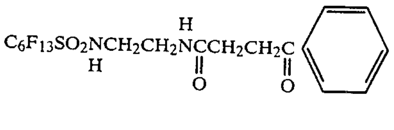
H

-continued

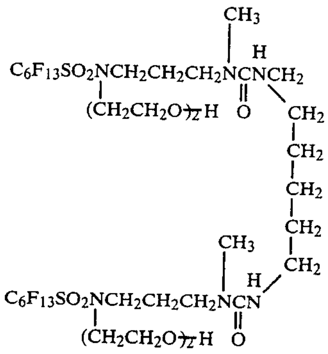
I

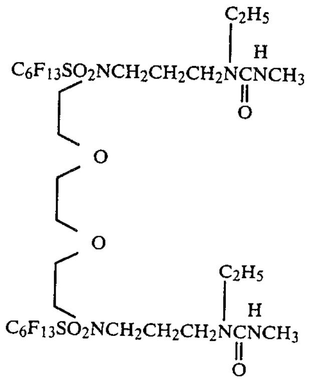
J

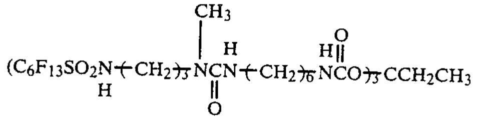
K

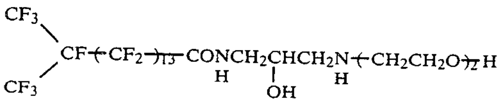
L

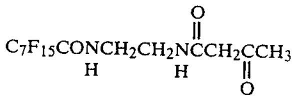
M

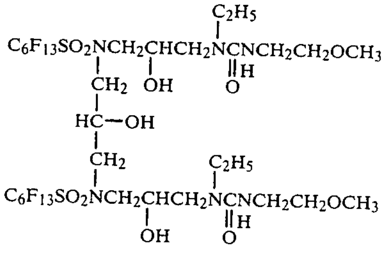
N

12. The method of claim 1 wherein an uranyl ion is recovered from sea water by adding a fluorine-containing compound within the general formula (I) and which has a high ability to selectively include the uranyl ion to the sea water in which the uranyl ion is dissolved or dispersed, and separating the uranyl ion from the sea water by including it in an ionophore formed by the fluorine-containing compound.

13. The method of claim 12 wherein said fluorine-containing compound is selected from the group consisting of:
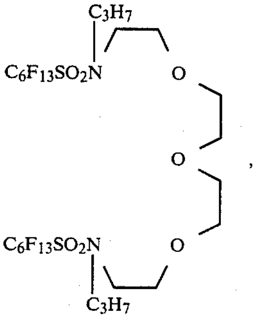
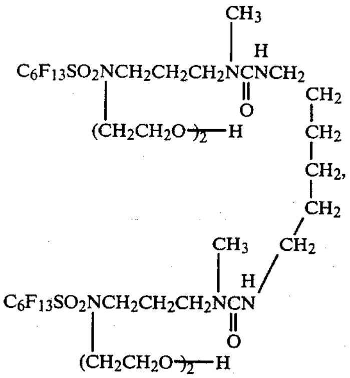
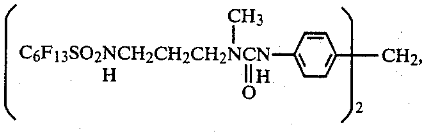
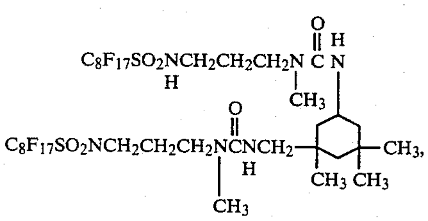
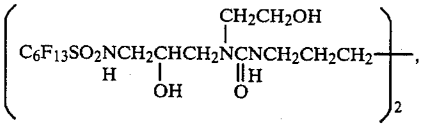
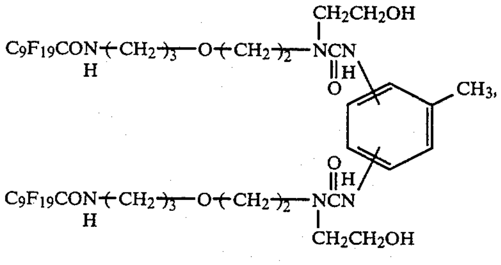
-continued
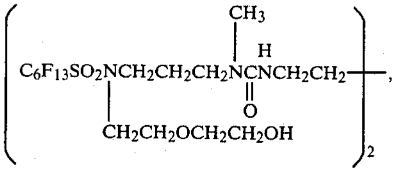
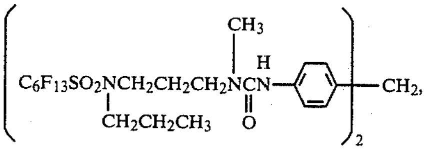
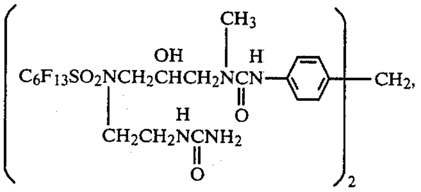
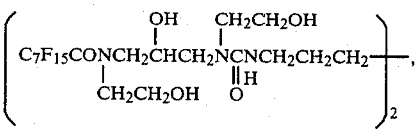
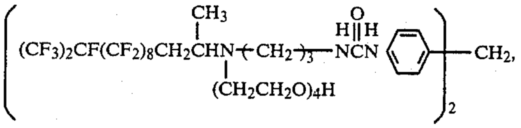
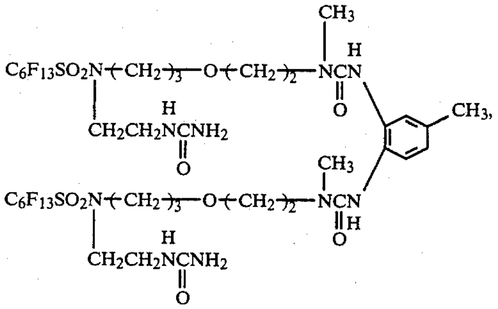
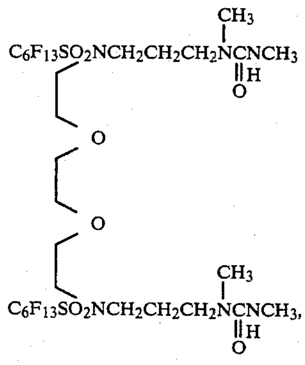

-continued
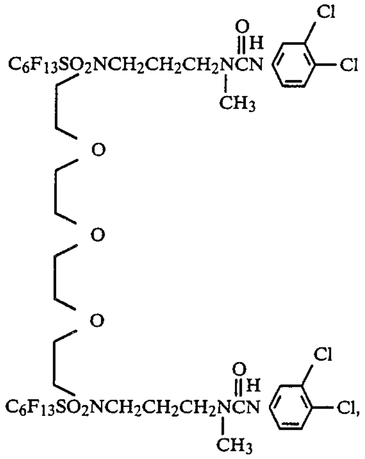
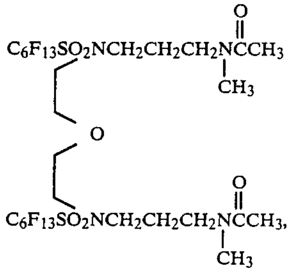
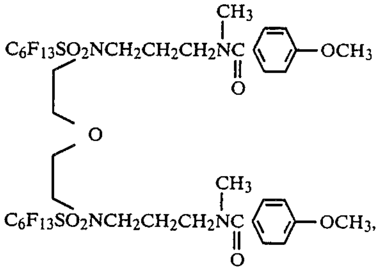
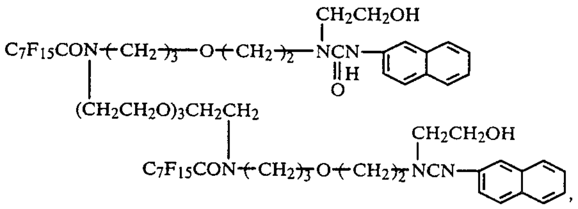
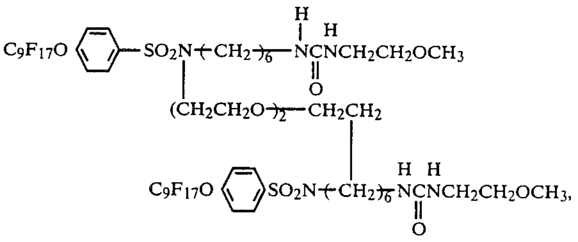
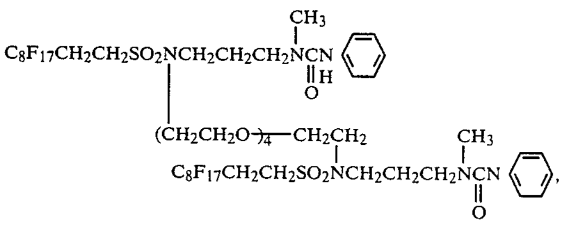
-continued
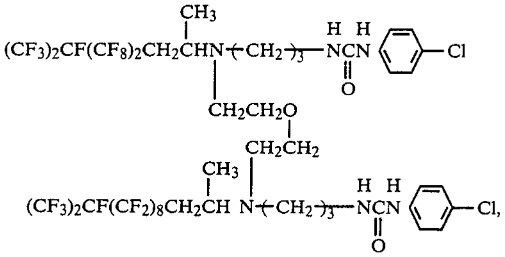
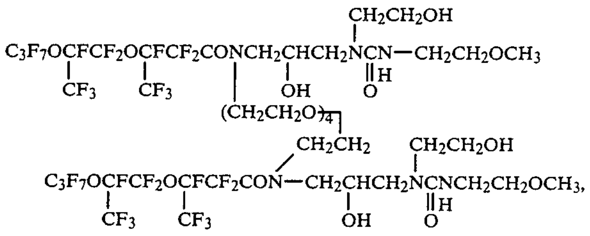
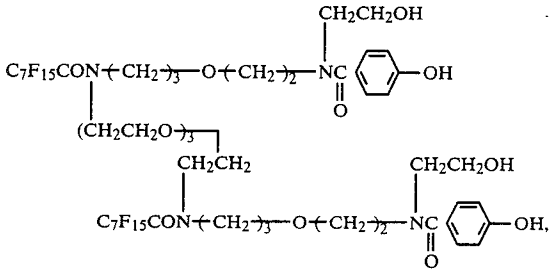
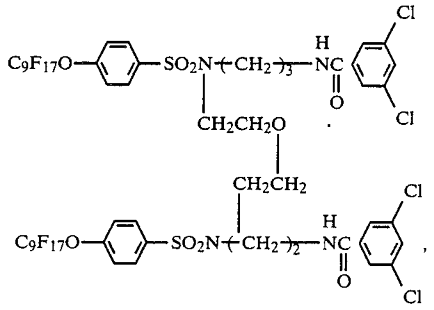
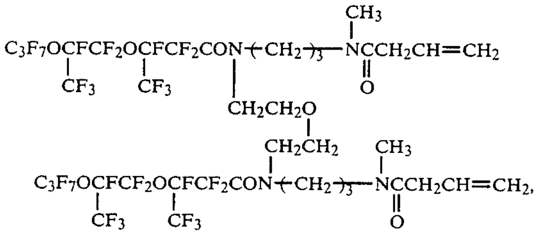
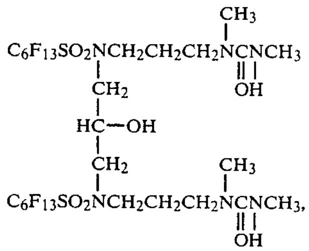
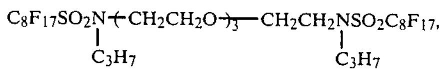

-continued
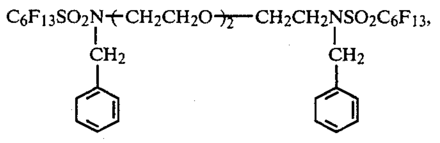
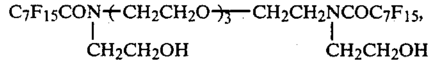
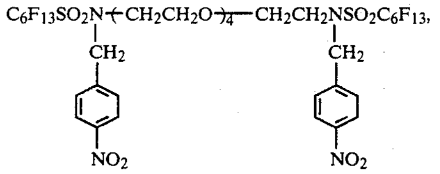
-continued
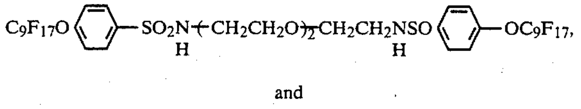
and
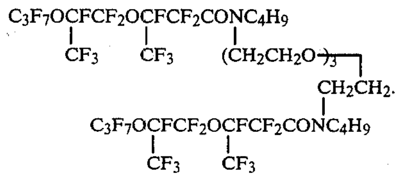
14. The method of claim 1 wherein said water-insoluble organic solvent has a solubility parameter, δ, of at least 7.5.
15. The method of claim 1 wherein said liquid medium is water.
* * * * *

UNITED STATES PATENT AND TRADEMARK OFFICE
CERTIFICATE OF CORRECTION

PATENT NO. : 4,486,391

DATED : December 4, 1984

INVENTOR(S) : Yutaka Hashimoto

It is certified that error appears in the above-identified patent and that said Letters Patent is hereby corrected as shown below:

Claim 7, line 12, delete the formula $-CH_2-CH-CH_2-$
$\phantom{-CH_2-CH}|$
$\phantom{-CH_2-C}OR_3$ and replace with $-CH_2CH_2\underset{H}{N}\underset{\underset{O}{\|}}{C}NH_2$.

Claim 7, line 20, delete the formula $-CH_2\underset{\underset{OH}{|}}{C}HCH_2-$ and replace with $-CH_2-CH-CH_2$.
$\phantom{-CH_2-C}|$
$\phantom{-CH_2-}OR_3$ Claim 13, column 61, delete second formula and replace with

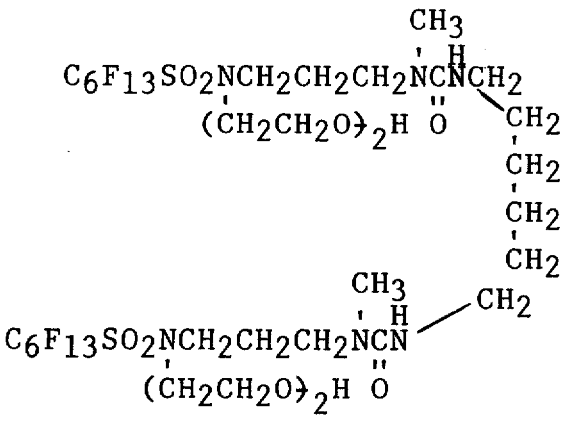

UNITED STATES PATENT AND TRADEMARK OFFICE

CERTIFICATE OF CORRECTION

PATENT NO. : 4,486,391

DATED : December 4, 1984

INVENTOR(S) : Yutaka Hashimoto

It is certified that error appears in the above-identified patent and that said Letters Patent is hereby corrected as shown below:

Claim 13, 17th formula (4th formula in column 63), delete formula and replace with

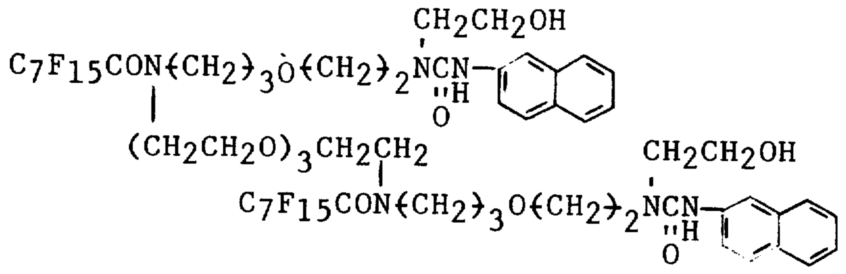

Claim 13, 18th formula (5th formula in column 63), delete formula and replace with

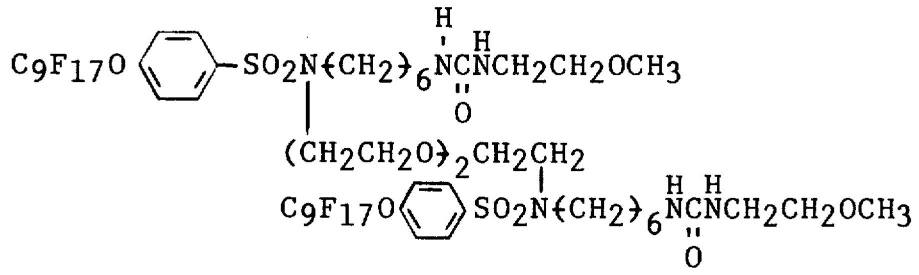

UNITED STATES PATENT AND TRADEMARK OFFICE

CERTIFICATE OF CORRECTION

PATENT NO. : 4,486,391

DATED : December 4, 1984

INVENTOR(S) : Yutaka Hashimoto

It is certified that error appears in the above-identified patent and that said Letters Patent is hereby corrected as shown below:

Claim 13, 19th formula (6th formula in column 63), delete formula and replace with

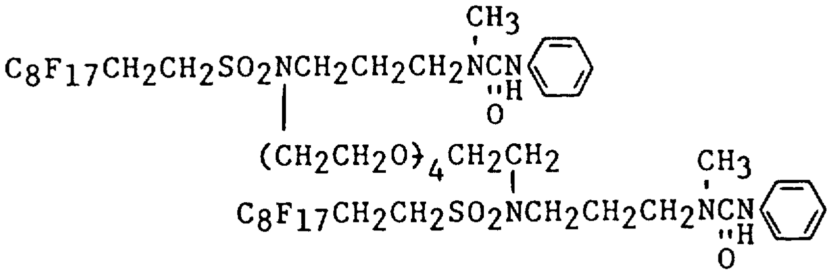

Claim 13, 23rd formula (4th formula in column 64), delete formula and replace with

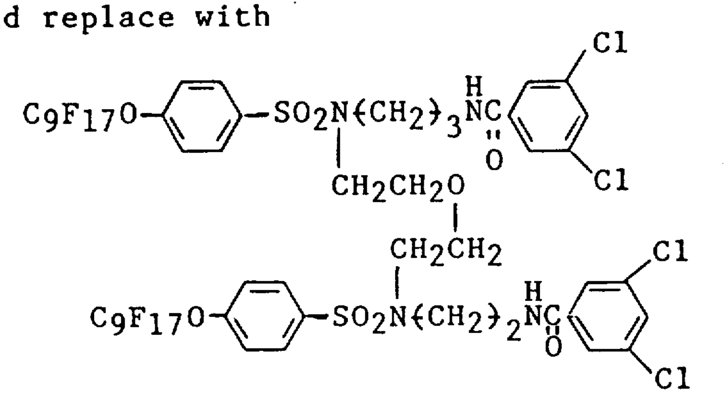

Signed and Sealed this

*Tenth* Day of *September 1985*

[SEAL]

*Attest:*

DONALD J. QUIGG

*Attesting Officer* *Acting Commissioner of Patents and Trademarks - Designate*